United States Patent
Bohmfalk

(10) Patent No.: US 6,237,596 B1
(45) Date of Patent: *May 29, 2001

(54) DISPOSABLE MASK AND SUCTION CATHETER

(76) Inventor: George L. Bohmfalk, 3 Pine Creek Pl., Texarkana, TX (US) 75503

( * ) Notice: Subject to any disclaimer, the term of this patent is extended or adjusted under 35 U.S.C. 154(b) by 0 days.

This patent is subject to a terminal disclaimer.

(21) Appl. No.: 08/849,920
(22) PCT Filed: Nov. 8, 1996
(86) PCT No.: PCT/US96/18350
  § 371 Date: Jun. 18, 1997
  § 102(e) Date: Jun. 18, 1997
(87) PCT Pub. No.: WO97/17034
  PCT Pub. Date: May 15, 1997

Related U.S. Application Data

(63) Continuation-in-part of application No. 08/555,148, filed on Nov. 8, 1995, now Pat. No. 5,694,927.

(51) Int. Cl.[7] .................................................. A62B 18/08
(52) U.S. Cl. ............................. 128/206.22; 128/206.19; 128/205.27; 128/206.21; 128/205.19; 128/911
(58) Field of Search ........................ 128/206.22, 206.19, 128/206.21, 201.23, 201.25, 910, 911, 205.12, 205.19, 205.21

(56) References Cited

U.S. PATENT DOCUMENTS

| | | | |
|---|---|---|---|
| 1,169,995 | * | 2/1916 | Prindle .......................... 128/205.19 |
| 1,169,996 | * | 2/1916 | Prindle .......................... 128/205.19 |
| 4,419,993 | * | 12/1983 | Peterson ........................ 128/201.15 |
| 4,469,097 | * | 9/1984 | Kelman .......................... 128/205.21 |
| 4,848,366 | * | 7/1989 | Aita et al. ..................... 128/206.19 |
| 4,951,662 | * | 8/1990 | Townsend, Jr. ................ 128/205.25 |
| 5,694,927 | * | 12/1997 | Bohmfalk ...................... 128/206.19 |
| 5,706,804 | * | 1/1998 | Baumann et al. ............. 128/206.19 |

* cited by examiner

Primary Examiner—Aaron J. Lewis
Assistant Examiner—V. Srivastava
(74) Attorney, Agent, or Firm—Falk & Fish llp; Robert Hardy Falk; Tommy Ray Vestal

(57) ABSTRACT

A disposable mask and suction catheter includes a mask having a front side and a back side, the back side being disposed in contact with a user's face during use. The disposable mask and suction catheter also includes a catheter tube having a first and a second end, the first end being removably attachable to a suction source for removing exhaled air and the second end being attached to the back side of the mask. The disposable mask and suction catheter helps to prevent fogging of glasses or other eyewear due to moist, exhaled air that escapes from behind the mask, and improves user comfort by constantly removing the warm, moist air behind and around the mask and drawing cool dry air into the mask.

39 Claims, 13 Drawing Sheets

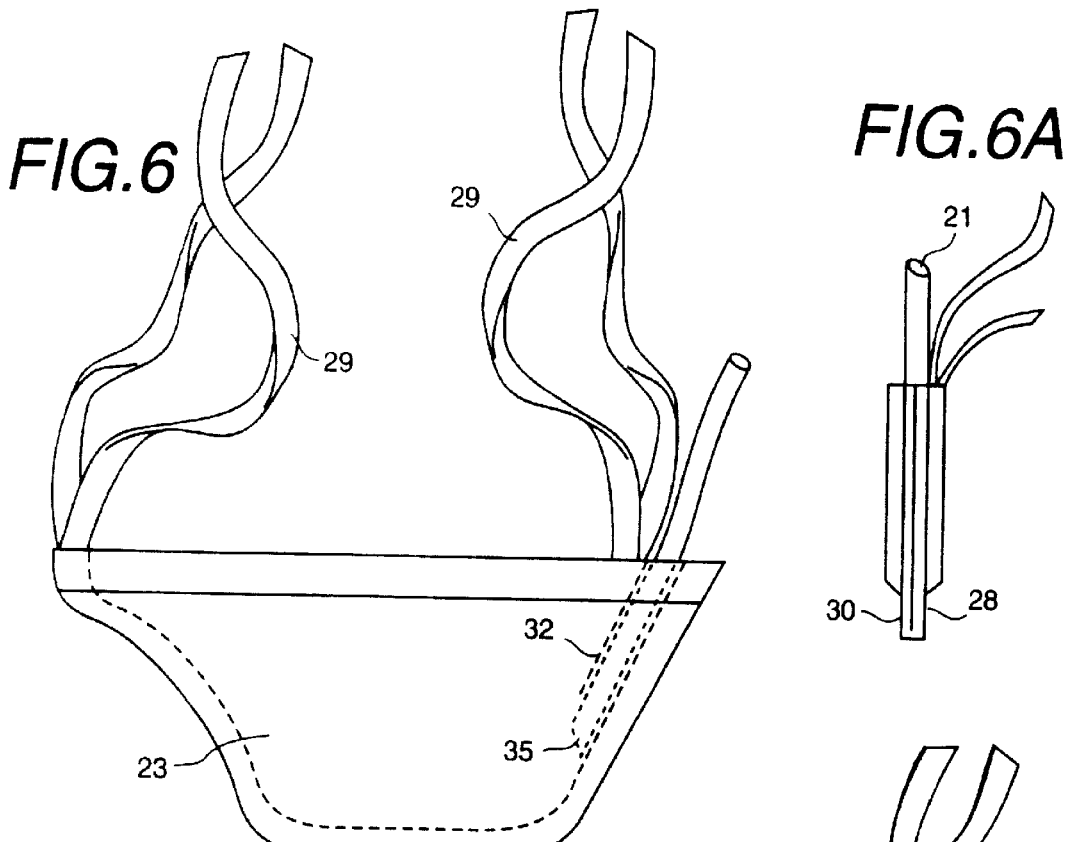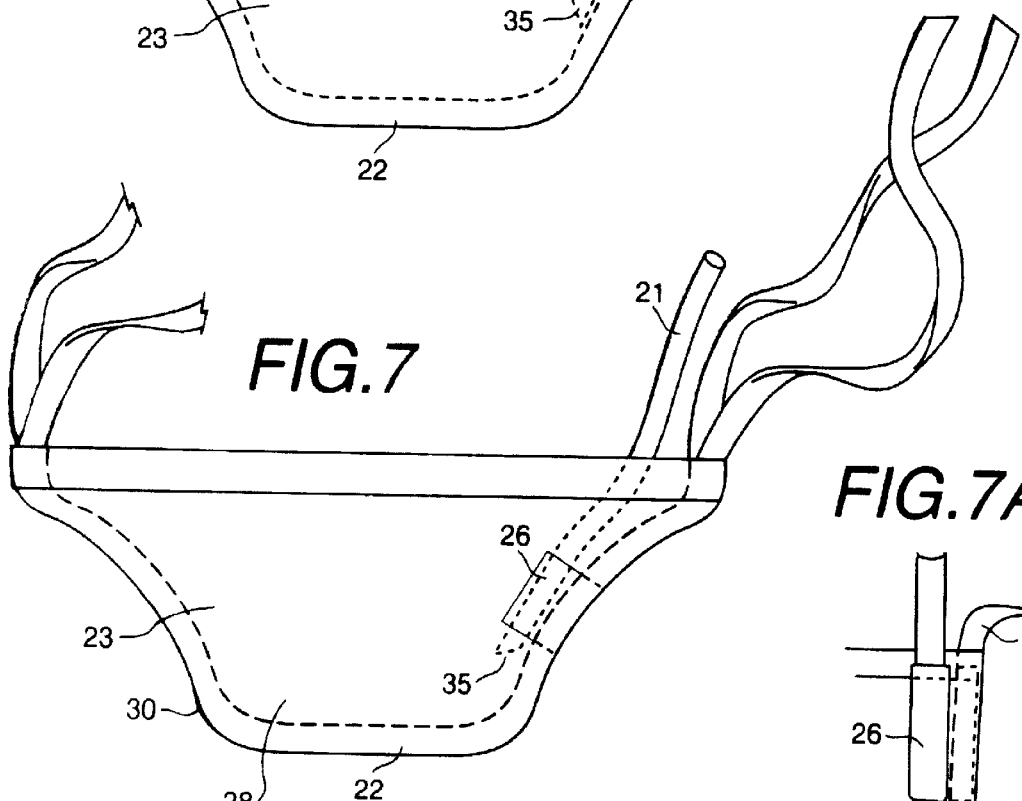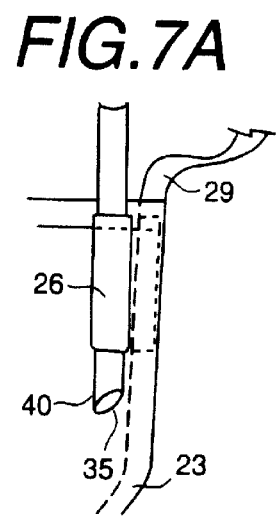

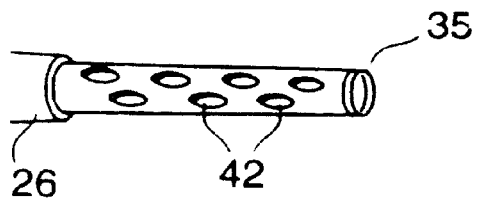
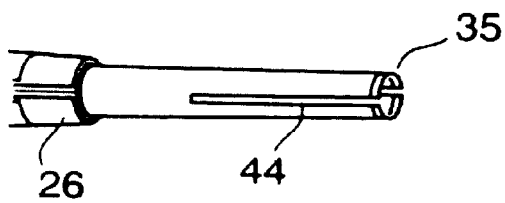
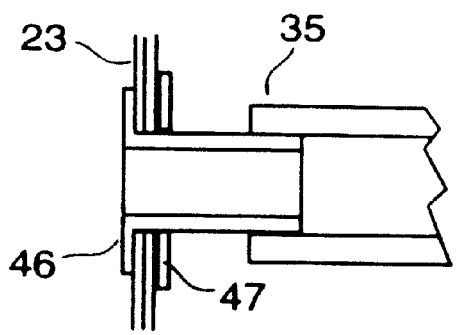
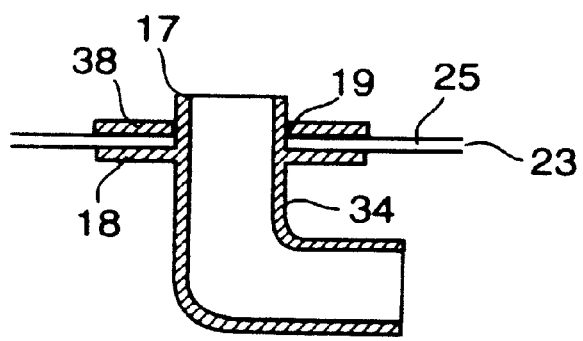

FIG. 11

| MASK | (1) P | (3) $N_0$ | (4) $\dfrac{\kappa}{\mu RT\lambda}$ | (5) @2mm $H_2O$ $V_0$ cm³/sec | Gurley Second $t$ |
|---|---|---|---|---|---|
| A | 1495.90 | $3.11 \times 10^{-2}$ | $1.03 \times 10^{-4}$ | 1153.60 | 3.43 |
| B | 1417.00 | $2.96 \times 10^{-2}$ | $9.8 \times 10^{-5}$ | 1097.60 | 3.60 |
| C | 354.96 | $7.39 \times 10^{-2}$ | $2.4 \times 10^{-5}$ | 268.80 | 14.43 |
| D | 1022.09 | $2.11 \times 10^{-2}$ | $6.98 \times 10^{-5}$ | 781.76 | 5.04 |
| E | 1326.20 | $2.75 \times 10^{-2}$ | $9.1 \times 10^{-5}$ | 1019.20 | 3.88 |
| F | 4610.72 | $9.6 \times 10^{-2}$ | $3.18 \times 10^{-4}$ | 3561.60 | 1.11 |
| G | 2361.23 | $4.93 \times 10^{-2}$ | $1.63 \times 10^{-4}$ | 1825.60 | 2.16 |
| H | 817.93 | $1.29 \times 10^{-2}$ | $4.26 \times 10^{-5}$ | 477.12 | 8.25 |
| I | 925.16 | $1.93 \times 10^{-2}$ | $6.38 \times 10^{-5}$ | 714.56 | 5.51 |
| J | 2627.07 | $7.06 \times 10^{-2}$ | $2.33 \times 10^{-4}$ | 2609.60 | 1.51 |
| K | 1763.57 | $3.69 \times 10^{-2}$ | $1.22 \times 10^{-4}$ | 1366.40 | 2.89 |
| L | 2350.65 | $4.91 \times 10^{-2}$ | $1.62 \times 10^{-4}$ | 1814.40 | 2.17 |
| M | 694.95 | $1.45 \times 10^{-2}$ | $4.79 \times 10^{-5}$ | 536.48 | 7.35 |
| N | 916.83 | $1.91 \times 10^{-2}$ | $6.32 \times 10^{-5}$ | 707.84 | 5.57 |
| O | 1359.02 | $2.84 \times 10^{-2}$ | $9.39 \times 10^{-5}$ | 1051.68 | 3.75 |
| P | 1231.27 | $2.57 \times 10^{-2}$ | $8.50 \times 10^{-5}$ | 952.00 | 4.15 |
| Q | 1294.66 | $2.7 \times 10^{-2}$ | $8.93 \times 10^{-5}$ | 1000.16 | 3.95 |
| R | 1049.53 | $2.19 \times 10^{-2}$ | $6.28 \times 10^{-4}$ | 703.36 | 4.86 |
| S | 1796.46 | $3.75 \times 10^{-2}$ | $1.24 \times 10^{-4}$ | 1392.38 | 2.84 |
| T | 796.98 | $3.75 \times 10^{-2}$ | $5.50 \times 10^{-5}$ | 616.90 | 6.41 |
| U | 416.37 | $1.49 \times 10^{-2}$ | $4.93 \times 10^{-5}$ | 552.16 | 7.12 |
| V | 753.04 | $1.57 \times 10^{-2}$ | $5.2 \times 10^{-5}$ | 582.40 | 6.77 |
| W | 3886.79 | $8.14 \times 10^{-2}$ | $2.69 \times 10^{-4}$ | 3012.80 | 1.31 |
| X | 1077.68 | $2.24 \times 10^{-2}$ | $7.41 \times 10^{-5}$ | 829.92 | 4.75 |
| Y | 1625.53 | $3.34 \times 10^{-2}$ | $1.10 \times 10^{-4}$ | 1232.00 | 3.19 |
| Z | 924.23 | $1.95 \times 10^{-2}$ | $6.45 \times 10^{-5}$ | 722.40 | 5.47 |
| AA | 877.42 | $1.83 \times 10^{-2}$ | $6.05 \times 10^{-5}$ | 677.60 | 5.82 |
| BB | 1443.71 | $3.02 \times 10^{-2}$ | $9.99 \times 10^{-5}$ | 1118.88 | 3.53 |
| CC | 1729.97 | $3.6 \times 10^{-2}$ | $1.19 \times 10^{-4}$ | 1332.80 | 2.95 |
| DD | 1691.09 | $3.53 \times 10^{-2}$ | $1.16 \times 10^{-4}$ | 1299.20 | 3.02 |
| EE | 1232.81 | $2.57 \times 10^{-2}$ | $8.5 \times 10^{-5}$ | 952.00 | 4.14 |

*FIG. 11A*

| MASK | TYPE | PERMEANCE | SUBJECTIVE BREATHABILITY | "AT REST" COMFORT LEVEL | ASPIRATING COMFORT LEVEL | | | | |
|---|---|---|---|---|---|---|---|---|---|
| | | | | | 5 Fr | 8 Fr | 10 Fr | 14 Fr | 18 Fr |
| A | C | 1495 | 2* | 3 | 0 | 3 | 4 | 4 | 4 |
| B | D | 1417 | 6* | 2 | 0 | 2 | 3 | 4 | 4 |
| C | D | 355 | 7* | 2 | 0 | 1 | 2 | 4 | 4 |
| D | C | 1022 | 4* | 2 | 0 | 2 | 2 | 4 | 4 |
| E | C | 1326 | 5* | 2 | 0 | 2 | 2 | 4 | 4 |
| F | Cn | 4610 | 1* | 2 | 0 | 2 | 2 | 4* | 4 |
| G | C | 2360 | 3* | 2 | 0 | 2 | 2 | 4 | 4 |
| H | C | 818 | 1 | 2 | 0 | 2 | 3 | 4 | 4 |
| I | C | 925 | 1 | 1 | 0 | 0 | 2 | 4 | 4 |
| J | Cn | 3537 | 3 | 2 | 0 | 3 | 4 | 4 | 4 |
| K | C | 1763 | 3 | 1 | 0 | 2 | 3 | 4 | 4 |
| L | C | 2360 | 3 | 2 | 1 | 2 | 3 | 4 | 4 |
| M | D,St | 694 | 1 | 2 | 0 | 1 | 3 | 4 | 4 |
| N | D,St,S | 916 | 1 | 1 | 0 | 2 | 3 | 4 | 4 |
| O | D,St | 1360 | 2 | 2 | 1 | 3 | 4 | 4 | 4 |
| P | C,L | 1230 | 2 | 3 | 0 | 1 | 3 | 4 | 4 |
| Q | C,L | 1294 | 2 | 2 | 0 | 1 | 3 | 4 | 4 |
| R | C,L | 1050 | 1 | 3 | 0 | 1 | 3 | 4 | 4 |
| S | C,Sh,T | 1796 | 2 | 2 | 0 | 1 | 2 | 4 | 4 |
| T | Cn | 796 | 2 | 1 | 0 | 1 | 2 | 3 | 4 |
| U | D,T | 716 | X | 3 | 0 | 1 | 3 | 4 | 4 |
| V | Cn | 753 | 2 | 1 | 0 | 1 | 2 | 3 | 4 |
| W | Cn | 3900 | 3 | 2 | 0 | 1 | 1 | 3 | 4 |
| X | C,Sh,T | 1077 | 2 | 1 | 0 | 1 | 2 | 4 | 4 |
| Y | D,T | 1625 | 2 | 2 | 0 | 2 | 3 | 4 | 4 |
| Z | C | 934 | 1 | 2 | 0 | 2 | 3 | 4 | 4 |
| AA | C | 877 | 1 | 2 | 0 | 2 | 3 | 4 | 4 |
| BB | C | 1443 | 2 | 2 | 0 | 2 | 3 | 4 | 4 |
| CC | C | 1730 | 3 | 2 | 0 | 1 | 2 | 4 | 4 |
| DD | C | 1700 | 3 | 2 | 0 | 1 | 2 | 4 | 4 |
| EE | C | 1232 | 2 | 2 | 0 | 2 | 3 | 4 | 4 |

C=Contour; Cn=Cone; D=Duckbill; Sh=Shield; St=Elastic Straps; T=Tie Strands; L=Ear Loops. All cone masks have elastic straps.

Masks A-G were ranked 1 to 7 in breathability and comfort, with 1 being the most comfortable and 7 being the least comfortable.

Mask U is of the prior art with differential permeabilities of the upper and lower portions, designed to deflect exhaled air out through the lower portion of the mask in hopes of avoiding fogging.

*FIG. 11B*

| | DEVICE AND DESCRIPTION |
|---|---|
| A | Technol® CareBear Surgical Mask, mfg. by Technol, Inc., Ft. Worth, TX, stock #47123-025; U.S. Pat. 4,673,084 |
| B | Technol® Duckbill Surgical Mask, mfg. by Technol, Inc., Ft. Worth, TX, stock #47124-010; U.S. Pats. 4,673,084; 4,606,341 |
| C | Technol® PFR95™ Particulate Filter Mask, mfg. by Technol, Inc., Ft. Worth, TX, stock #47119-170; U.S. Pats. 4,920,960; 5,322,061; Des. 347,713; addtl. pats. pend. |
| D | Technol® Lazer™ Surgical Mask, mfg. by Technol, Inc., Ft. Worth, TX, stock #47128-020 |
| E | Johnson & Johnson Surgine™ II Face Mask, mfg. by Johnson & Johnson Medical, Inc., Arlington, TX, cat. #4230 |
| F | 3M Aseptex™ 1800+ Molded Surgical Mask, mfg. by 3M Health Care, St. Paul MN, cat. #1800+ |
| G | 3M Tie-On Surgical Mask, mfg. by 3M Health Care, St. Paul MN, cat. #1818 |
| H | Technol® FLUIDSHIELD® Surgical Mask, mfg. by Technol, Inc., Ft. Worth, TX, stock #47123-070; U.S. Pats. 4,673,084; 4,920,960; 4,969,457; 5,020,533; 5,150,703; 5,383,450; 4,635,628; addtl. pats. pend. |
| I | Technol® FLUIDSHIELD® Surgical Mask, with Wrap-around SplashGuard® Visor, mfg. by Technol, Inc., Ft. Worth, TX, stock #47123-080; U.S. Pats. 4,920,960; 5,020,533; 5,150,703; 5,383,450; 5,406,943; Des. 355,485; addtl. pats. pend. |
| J | Technol® Cone Classic™ Surgical Mask, mfg. by Technol, Inc., Ft. Worth, TX, stock #47121-010; pat. pend. |
| K | Technol® Ulti-Mask™ , mfg. by Technol, Inc., Ft. Worth, TX, stock #47129-010 |
| L | Technol® The Lite One® Surgical Mask, mfg. by Technol, Inc., Ft. Worth, TX, stock #47125-010 |
| M | Technol® PCM2000™ Sub-micron FLUIDSHIELD® Face Mask, mfg. by Technol, Inc., Ft. Worth, TX, stock #47118-070; U.S. Pats. 4,920,960; 4,969,457; 5,322,061; Des. 347,713; addtl. pats. pend. |
| N | Technol® PCM2000™ High Filtration FLUIDSHIELD® Face Mask with Wraparound TopGuard™ Visor; mfg. by Technol, Inc., Ft. Worth, TX, stock #47118-085; U.S. Pats. 4,969,457; 4,920,960; 5,150,703; 5,020,533; addtl. pats. pend. |
| O | Technol® PCM2000® Sub-micron Face Mask, mfg. by Technol, Inc., Ft. Worth, TX, stock #47118-010; U.S. Pat. 5,322,061; Des. 347,713 |
| P | Technol® Fog-Free™ High Filtration Earloop Mask, mfg. by Technol, Inc., Ft. Worth, TX, stock #50512; U.S. Pats. 4,635,628; 4,802,473; 4,941,470 |
| Q | Technol® SoSoft™ Procedure™ Mask, mfg. by Technol, Inc., Ft. Worth, TX, stock #50500; U.S. Pat. 4,673,084 |

FIG. 11B(a)

| | |
|---|---|
| R | Technol® Procedure™ Mask, mfg. by Technol, Inc., Ft. Worth, TX, stock #50104; U.S. Pats. 4,802,473; 4,941,470 |
| S | 3M Tie-On Surgical Mask with Face Shield, mfg. by 3M Health Care, St. Paul MN, cat. #1818FS; U.S.Pat. 4,816,333 |
| T | 3M Healthcare Particulate Respirator, mfg. by 3M Health Care, St. Paul MN, cat. #1814 |
| U | 3M Filtron™ High Performance Surgical Mask, mfg. by 3M Health Care, St. Paul MN, cat. #1838 |
| V | 3M Aseptex™ Sub-Micron Molded Surgical Mask, mfg. by 3M Health Care, St. Paul MN, cat. #1812 |
| W | Johnson & Johnson Surgine™ II Cone Mask, mfg. by Johnson & Johnson Medical, Inc., Arlington, TX, cat. #4235 |
| X | Johnson & Johnson BARRIER™ Extra Protection PLUS Mask, mfg. by Johnson & Johnson Medical, Inc., Arlington, TX, cat. #4232 |
| Y | Johnson & Johnson Surgine™ II Soft Arch Mask, mfg. by Johnson & Johnson Medical, Inc., Arlington, TX, cat. #4233 |
| Z | Johnson & Johnson BARRIER™ Laser Plume Mask, mfg. by Johnson & Johnson Medical, Inc., Arlington, TX, cat. #4236 |
| AA | Johnson & Johnson Surgine™ Fashion Mask, mfg. by Johnson & Johnson Medical, Inc., Arlington, TX, cat. #4237 |
| BB | Johnson & Johnson Surgine™ Face Mask, mfg. by Johnson & Johnson Medical, Inc., Arlington, TX, cat. #4239 |
| CC | Johnson & Johnson Surgine™ Anti-Fog Mask, mfg. by Johnson & Johnson Medical, Inc., Arlington, TX, cat. #4238 |
| DD | Johnson & Johnson Surgine™ II Anti-Fog Mask, mfg. by Johnson & Johnson Medical, Inc., Arlington, TX, cat. #4231 |
| EE | Johnson & Johnson BARRIER™ Extra Protection Face Mask, mfg. by Johnson & Johnson Medical, Inc., Arlington, TX, cat. #4234 |

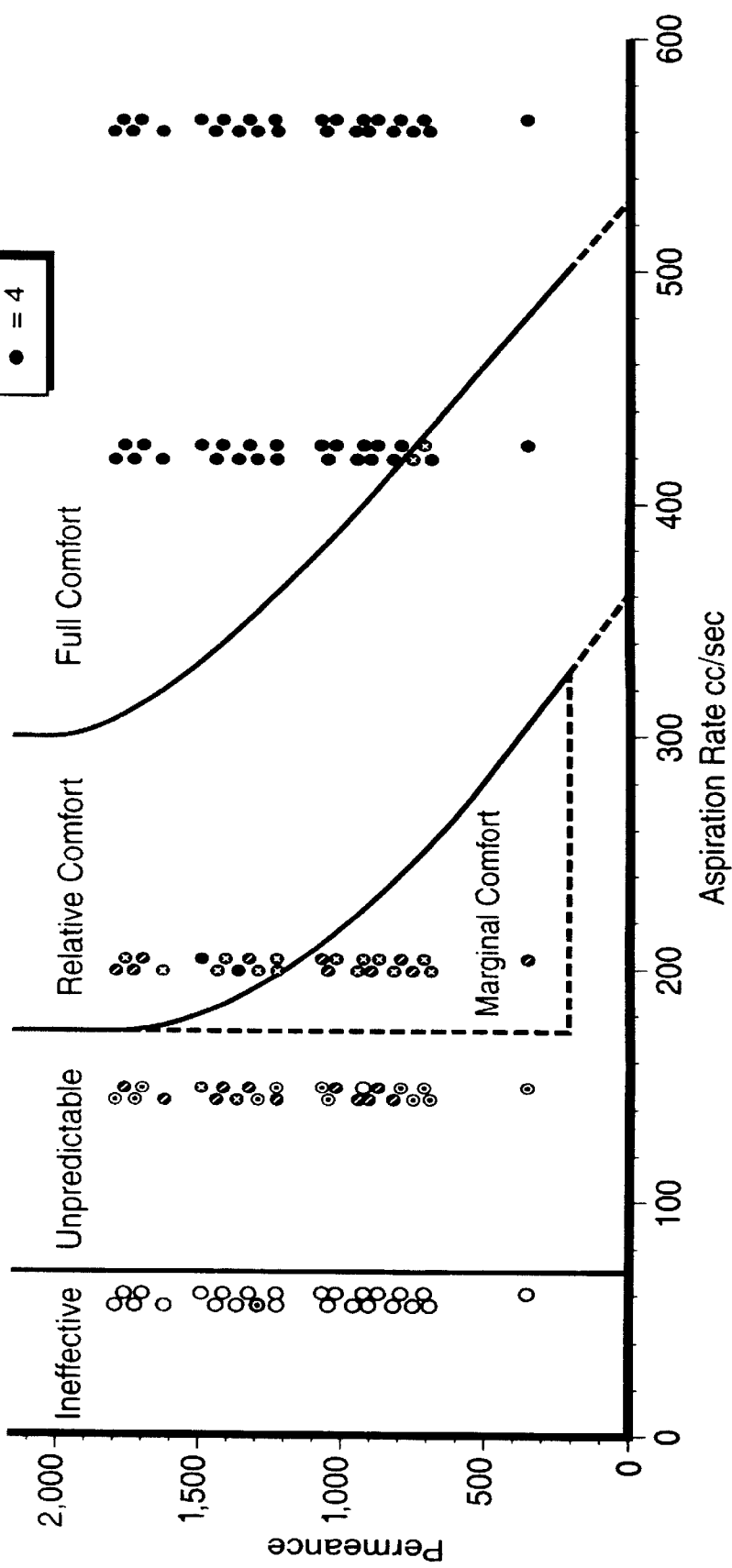

DISPOSABLE MASK AND SUCTION CATHETER

CROSS REFERENCE TO RELATED APPLICATION

This Application is a National Phase Application of PCT International Application No. PCT/US96/18350, filed Nov. 8, 1996, which claims priority as a Continuation-In-Part to U.S. application Ser. No. 08/555,148, filed Nov. 8, 1995 and entitled "Disposable Mask And Suction Catheter," and which issued as U.S. Pat. No. 5,694,927 on Dec. 9, 1997.

TECHNICAL FIELD

The present invention relates generally to surgical-type masks and, more particularly, to disposable surgical-type masks having a suction device associated therewith for removing exhaled air from behind the mask.

BACKGROUND ART

Surgeons typically wear face masks designed primarily to prevent contamination of the surgical field and wound by bacteria and other infectious particles borne in the surgeon's breath and on the face and facial hair. These masks generally cover the wearer's nose, mouth, chin, and medial aspects of the cheeks. Formerly, these were made of cloth and were washed, sterilized, and reused many times. The era of comparatively inexpensive disposable materials led to these masks being made of some type of paper (cellulosic) fiber or combination of thermoplastic films and fibers and thus becoming single-use, disposable items.

A commonly used mask features a horizontally pleated rectangle of porous paper with 12"–14" (30.5–35.6 cm) long paper-string tie strands at each corner. The tie strings are used to tie the mask behind the neck and over the top of the head of the wearer. The lateral edges of the mask usually conform rather loosely to the sides of the wearer's cheeks. This fit is dependent on the tightness to which the wearer ties the strands, whether the mask is tied according to the intent of the design, and the general shape of the wearer's face. Bands of thin metal or other malleable material are often fabricated into the upper edge of the mask to allow molding of this edge to the contour of the upper nose.

Masks of this invention preferably are made of somewhat permeable material, in that expired air may pass through the mask, ideally filtering out aerosol particles in the expired air to prevent their contaminating the surgical wound. However, if the mask is not applied according to design; if the wearer ties the strands loosely; if the malleable band is not molded to the contour of the upper nose; or if the wearer's face is particularly thin, there may be relatively free flow of air around the edges of the mask. Commonly, a substantial portion of the air expired by the wearer passes out around the mask, generally at either side and out the upper edge, as the mask fits rather loosely and is not sealed to the wearer's skin. This is associated with at least three problems:

1) the exhausting of expired air around the edges of the mask exposes the surgical operating zone to contamination by aerosolized particles in this unfiltered air,
2) the warm, humidified expired air emerging through the upper edge of the mask tends to fog the wearer's eyeglasses and operating microscopes because the relative humidity of the wearer's exhaled air exceeds the dew point of the air in the operating room, impairing the surgeon's visibility, and
3) rebreathing the warm, moist $CO_2$-laden air wears on the stamina of the wearer.

The second problem, of fogging eyeglasses and microscopes, has been typically dealt with by affixing adhesive tape along the upper edge of the mask to the wearer's upper nose and cheeks to create a seal. The warm, humid air is then directed out laterally. However, due to perspiration and secretion of skin oils, this tape seal often deteriorates during the course of an operation, with attendant loss of seal and resultant fogging. Additionally, removal of this tape from the skin after each operation can be very uncomfortable and results in painful tape irritation, especially when this may be done several times a day in the course of multiple operations. Moreover, the surgeon is often uncomfortable during surgery, and fatigue tends to occur more quickly.

Such problems with known surgical masks have, in the past, been addressed in several ways. One solution has been to reduce the temperature in the operating room so that the surgeons do not feel as hot and perspire. This solution, however, presents risk of complication for the patient from lowered body temperature, particularly during long operations, and causes discomfort for others in the operating room, such as nurses and anesthesia crew members, who often must wrap themselves in blankets and extra gowns to avoid freezing.

Another solution has been to provide a portable suction device or exhaust fan that can be attached to the surgeon's mask to constantly evacuate exhaled air and draw fresh air into the mask. Such devices have, however, involved many parts and have been rather cumbersome. Further, these types of devices exhaust into the operating room with the concomitant problems of such exhausting.

In recent years, an additional concern has arisen which is just beginning to be addressed by mask manufacturers. The specter of emerging antibiotic-resistant organisms and HIV has introduced the additional consideration of transmission of infectious diseases from the patient to the health care worker. One obvious portal of entry of infective particles to the health care worker is around the loose-fitting edges of a face mask. Mask manufacturers are developing and marketing model masks designed to minimize this risk. These masks entail a much more secure fit of mask to face to eliminate the open spaces around the edges. However, this solution to one problem exacerbates another, in that the tighter-fitting, presumably safer, masks trap more expired air about the face in the enclosed zone between the mask and face. This warm, moist air becomes uncomfortable to the wearer and may even contribute to a sense of fatigue. Furthermore. as the moisture accumulates on the inner surface of the mask, bacterial growth is enhanced and the effectiveness of the mask as a filter diminishes as the breathing passages of the mask material become clogged with moisture.

Outside of the context of surgery, similar problems to those discussed above are experienced where, for whatever reason, one must wear corrective or protective goggles and some manner of protective face mask at the same time, such as for work in dusty environments, where the phenomenon of fogging glasses due to exhaled air tends to occur. In other areas of critical care within a hospital, such as intensive care units, pediatric and neonatal units, transplantation units, chemotherapy units, infectious disease including AIDS units, and other areas where infection of both patient by the care giver and the care giver by the patient is a particular concern, workers have experienced problems with fogging of eyeglasses while wearing protective masks. In research, medical, forensic, or scientific laboratories where protective masks are indicated or desired, either for protection of the worker from experimental agents or protection of the experimental animals and materials from contamination by the worker, similar problems are experienced.

In industrial "clean rooms", such as are required in many high technology fields such as aerospace, computer, electronic, pharmaceutical, medical diagnostic and other biomedical industries, face masks are commonly required of workers to prevent contamination of the product by the worker. Such workers experience the problems enunciated above as well. There is, accordingly, a need for some way of simply and inexpensively minimizing the effects of exhaled air behind masks, such as discomfort and fogged lenses, without the need for lowering room temperatures.

Attempts to satisfy the addressed shortcomings have also had shortcomings. U.S. Pat. No. 3,130,722 to Dempsey, et al., describes an unconventional and impervious mask with fixed vent holes 26 and having an exhaust tube 34 attached to the mask via a nipple connection 30 located in a reinforced section 25 of the mask. The exhaust means in FIG. 1 is a pneumatically-driven exhaust fan. Other exhaust means described in column 4 fail to appreciate the specific relationships between the elements set forth in the present invention..

U.S. Pat. No. 5,054,480 to Bare, et al., describes a headgear to be worn by physicians during a surgical procedure comprising fans for introducing air about the head and face through a complicated system of channels, and an exhaust fan to draw air from the face area. A shroud or hood is draped over the headgear forming a window for viewing. The headgear circulation system is cumbersome to the wearer and difficult to clean for reuse. While such complicated apparatus may be necessary in certain extreme conditions, the vast majority of uses do not require such complexity.

U.S. Pat. No. 4,951,662 to Townsend, Jr., discloses a mask as part of an air circulation loop to create user comfort and eliminate eyeglass fogging. Air chamber tubes 12 and 13 are attached to an air contour plate 11 fitted inside a mask 10, securing the mask to the chamber tubes. The tubes are used to expand the effective volume between the face and mask. A fan 14 located behind the wearer's head recirculates air through the mask in a circular fashion. The fan appears to recirculate exhaled air, as well.

U.S. Pat. No. 4,848,366 to Aita, et al. discloses an impervious surgical mask that may be opaque or clear. The mask has an opening or passageway 23 on both sides. An exhaust tube 26 and a battery-operated exhaust fan 62 is mounted in one opening. The exhaust fan may be mounted directly to the mask. The teaching of Aita, et al. are that the front portion 22 of the mask should be stiff to promote flow of air through the cavity formed by the mask and the face of the wearer. A difficulty with this type of concentrated flow can be the noise level of the air movement. The efficiency of use of the air in scavenging the full mask area can also be a problem.

European Patent Publication 0 018 805, published Nov. 12, 1980 (Douglas) describes an apparatus for controlling exhaled breath from the nose and mouth of a wearer, including a molded, rigid transparent plastic face shield 10 shaped to extend around the lower front portion of the user's face. The shield has a plastic bead 9 to provide an airtight fit. Straps hold the shield in place about the wearer's face. On each side of the shield are outlet coupling members 12 to connect flexible suction conduits 13 at one end. To the other end of the flexible conduit is a motor-driven rotary suction impeller and housing (exhaust fan) to exhaust exhaled breath from the mask. Air enters along the upper edge 11 of the mask.

U.S. Pat. No. 3,890,966 to Aspelin, et al., describes a pervious mask with a sheet of air-impervious sheet material along the upper portion of the mask. The impervious sheet material has slits therein, cut in a manner to direct exhaled air through the slits away from the eyes of the wearer. There is lacking any appreciation for the overall sense of comfort afforded the wearer in the present invention.

All of these problems may be solved by incorporating a simple method to vacuum away, or scavenge, the wearer's expired breath with apparatus readily available in hospital operating rooms. The humid, potentially infectious air may be continuously eliminated from the operative area, and with it the problems of fogging, heat buildup and fatigue, and risk of transmitting infection to or from the patient.

DISCLOSURE OF INVENTION

The present invention is directed to the use of the combination of a disposable mask and a suction catheter tubing adapted to be connected with or to a vacuum (suction) source for removing exhaled air from the area between the mask and the face of the mask wearer. Preferably, the mask is of permeable material or layers of Ipermeable or porous material formed to fit closely to the face at the edge of the material. The material for the mask should be lightweight and porous, preferably with a mask material having an air permeance across the mask face of between about 350 and 4600 $m^{-6}/Pa.S$ and filtration capabilities to about $1\mu$ particle size. The mask surface area is about 200–300 $cm^2$. The effective mask area will be less, in the range of 40–100 $cm^2$, depending on the construction and the facial configuration of the wearer, and more specifically, not only how the mask is constructed, but how it fits the contours of the face of the user.

It is an object of this invention that the mask be usable for inhaling and exhaling air of the wearer conventionally, or without the operation of the suction source. The inclusion of the vacuum removal in the operation of the mask, however, will aid to prevent build-up of moisture within the mask and also to guard against exhaled moisture fogging the lens of the glasses or microscope being worn by the wearer.

The vacuum source contemplated in this invention is that available as part of a standard operating room theater. These vacuum sources are commonly wall or ceiling ports which may then be connected directly to the suction catheter tubing attached to the mask instead of the use of wheeled mobile vacuum units. By catheter tubing, it is meant flexible plastic tubing of small bore (8 French-20 French, or 1.6 mm–4.0 mm internal diameter) such as used in hospitals as suction tubing for fluids from surgical cavities and canals of a patient. The walls of such tubing are thin, but sufficient to withstand the vacuum forces exerted. For purposes of economics, the segments of connector tubing beyond the segment attached to the mask may be reused, inasmuch as the direction of flow is constantly away from both the wearer and the patient. Furthermore, if multiple individuals wish to utilize the present invention during the same operation, their individual connector tubings may be joined using appropriate connection "Y" or "tee" devices to the suction source.

The important feature of the present invention is the conjoining of two standard, inexpensive disposable items into a single, inexpensive, disposable mask assembly for the primary purpose of eliminating the problem of fogging glasses and surgical microscopes during the surgical operations. The device of the invention may be sold as one unit or a kit comprising a disposable mask and a catheter tube, preferably of a predetermined length and of an internal diameter of 8–14 French (1.6–2.8 mm), the tube adapted to be received at one end in the mask and on the other end adapted to be connected to the hospital vacuum supply source. The present invention is novel in its disposability, lightweight and simplicity. It is surprising that small tubing of the type contemplated can remove substantial quantities of air, creating the comfort of wear found in the mask herein. Advantages of the present invention are that a surgeon may easily avoid or minimize the aforementioned problems by using this mask with no special or extra effort required and at a minimal increased expense. Although the wearer is attached to the connector suction tubing, limiting somewhat his movement far from the operations area, most surgeons who would use this mask already wear headlights which are connected to power sources with equally restrictive mobility. The present invention provides the advantages noted without the additional weight requirements of exhaust fans, ducting bulkiness, expensive/nondisposable helmets which cannot be shared by multiple users, or which become infected with time, and the like of the prior art.

The present invention has surprisingly produced a cooler, drier air for inspiration by the wearer, producing a general sense of less fatigue and greater comfort for the wearer during long operations.

An advantage from the use of the instant invention is that through the scavenging of the humid, expired air, there is no moisture build-up within the mask as typically occurs with the standard mask without the vacuum removal device. This warm moisture build-up facilitates the multiplication of bacteria and other infectious agents within the mask during operations. Elimination of this warm moisture build-up minimizes multiplication of bacteria and other infectious agents within the mask and the concurrent risk of contaminating the patient with such organisms during usage.

In utilizing the vacuum source available in operating rooms and expelling the exhaled gases outside the operating room, the present invention has bypassed the difficulties of those earlier devices which merely direct unfiltered exhausted gases back into the operating room atmosphere. The use of the in-line liquid collection means with the vacuum source traps moisture exhaled and directs it from the system.

In accordance with one preferred aspect of the present invention, a disposable mask and a short length of suction catheter tubing is provided. The disposable mask and suction catheter tubing includes a mask having a front side and a back side, the back side being disposed in contact with a user's face during use. The edges of the mask form substantially a seal around the face so that expelled airborne particles on exhalation are forced into the mask or aspirated by the vacuum tubing. The disposable mask and suction catheter also include a catheter tubing having a first end and a second end, the first end being removably attachable to a suction source for exhausting exhaled air and the second end being in communication with the back side of the mask.

A disposable surgical type mask described herein comprises, preferably, at least one layer of pervious material having a surface area of about 200–350 cm$^2$ and air permeance of between about 350 and 4600 m$^{-6}$/Pa.S, malleable means for forming an upper portion of the mask about the wearer's nose and upper cheek and means for attaching the mask to the face area of the wearer. The mask also includes means for attaching one end of a suction catheter tubing of at least about 8–20 French diameter (1.6–4.0 mm i.d.) catheter in the zone between the inner surface of the mask and the face of the wearer, the other ending being removably attached to a predetermined suction force, preferably of between about 12 to about 20 inches Hg.

Also disclosed is a method of removing moist, stale air from the inside of a disposable surgical type mask, the method comprising placing the second end of a tubing catheter between the face of the mask wearer and the mask in a zone between the face of the mask wearer and the mask and connecting the first end to a predetermined vacuum source, preferably of between about 12 to about 20 inches Hg.

BRIEF DESCRIPTION OF THE DRAWINGS

The features and advantages of the present invention are well understood by reading the following detailed description in conjunction with the drawings in which like numerals indicate similar elements and in which a disposable mask and catheter tube according to an embodiment of the present invention is shown schematically:

FIG. 6 and FIG. 6A show further details of the FIG. 3 embodiment.

FIG. 7 and FIG. 7A depicts one form of attachment of the tubing to the mask.

FIG. 8 and FIG. 8A depict alternative treatment of the ends of the tubing.

FIG. 9 and FIG. 10 depict alternate attachment of the tubing to the inner part of the mask.

FIGS. 11, 11 A, 11B and 11B(*a*) are charts of mask evaluations using the invention herein.

MODES FOR CARRYING OUT THE INVENTION

Figure 1:
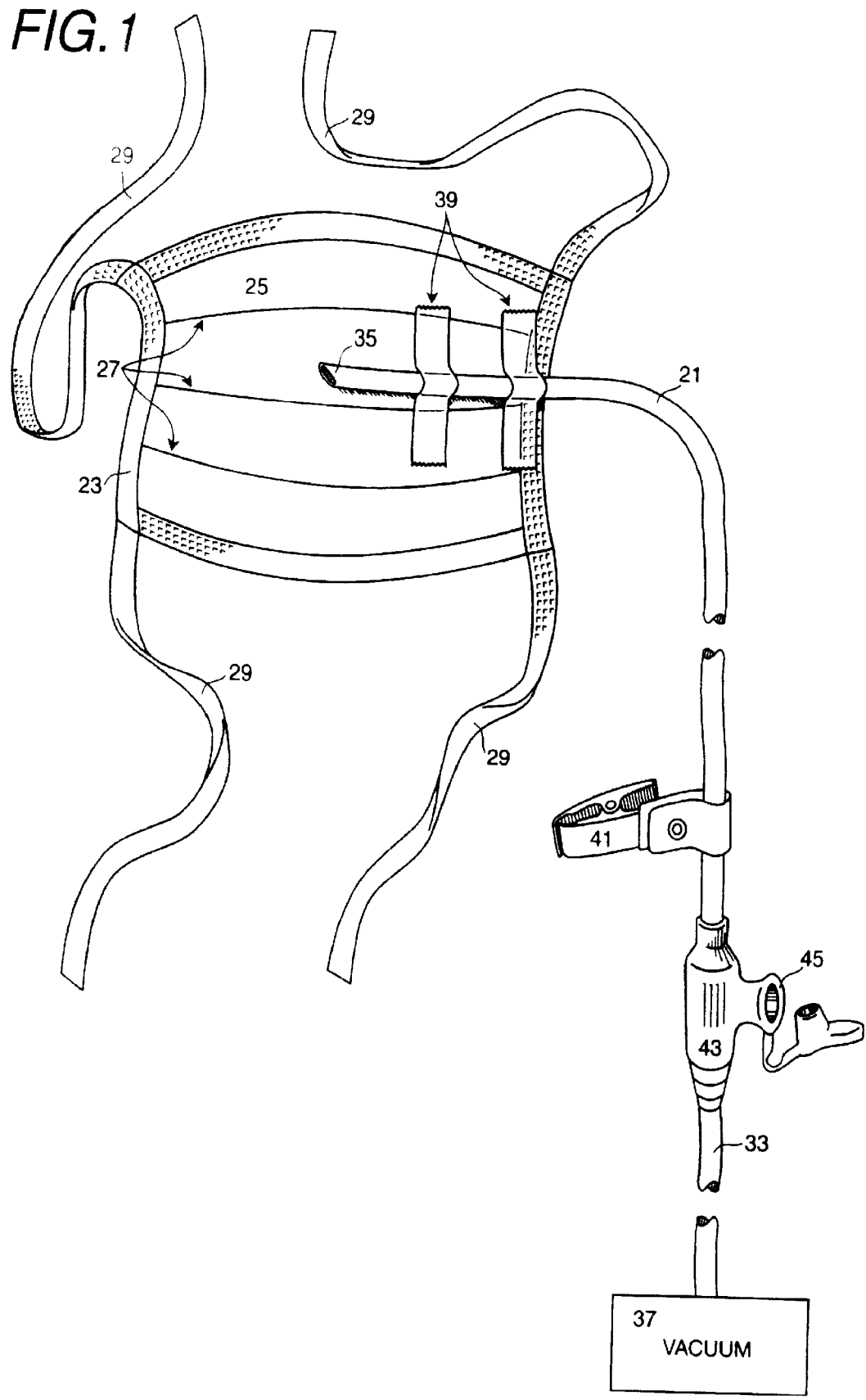
FIG. 1 depicts one embodiment of the invention.

In FIG. 1, a disposable mask and suction catheter 21 according to a preferred embodiment includes a mask 23 having a front side (not shown) and a back side 25. As will be explained in more detail below, the back side 25 is to be disposed in contact with a user's face during use. The mask 23 is preferably of a generally conventional configuration, such as of the type used as a surgical mask or for protection in dusty or otherwise hazardous environments in which pervious masks can be utilized. As shown in the drawing of FIG. 1, the mask 23 is formed from a sheet of material such as cotton or other pervious material having a plurality of pleats 27 to permit comfortable application of the mask over the face, and a number of tie cords or straps 29 attached to the sheet material. The mask may be formed of layers of material as disclosed in U.S. Pat. No. 4,920,960 to Hubbard, et al., the disclosure of which is incorporated herein by reference.

The disposable mask and suction catheter also includes a catheter tube 31 having a first end 33 and a second end 35. The first end 33 is removably attachable to a vacuum source 37 for removing exhaled air. The second end 35 is in communication with the back side 25 of the mask 23. In order to prevent a connector tubing 36 from exerting a drag on the catheter 21 of the present invention, it may be necessary to affix the first end of the suction catheter to the wearer's surgical gown or other clothing. This can be done by securing with standard adhesive tape or other means a clip 41 similar to that used by hospital personnel department to attach identification badges to employee's clothes. The clip is preferably attached proximate the first end of the suction catheter. Said second end 35 may have single or multiple openings for aspiration of air from the area between the wearer's face and the mask. Said catheter may have attached near to its first end 33 a device such as a clip 41 for removably attaching the first end 33 to the wearer's clothing in order to prevent the connector tubing from exerting a drag on the catheter first end 33. The first end 33 of the catheter would itself be fashioned to allow connection to sections 36 of larger standard vacuum tubing, preferably about 5 mm. The opposite or suction source end of the connector tubing 36 would then be attached to a standard hospital suction or vacuum source with a force of approximately 12–20 inches Hg. Intermediate the connector tubing 36 and wall outlet 37 may be a liquid collection device (not shown), including flow control valves. An example of such collection device is a Guardian tandem series canister assembly (Canister No. 64-3480A) manufactured by Baxter Healthcare Inc., Pharmaseal Division, Valencia, Calif. 91355-8900.

Variable relationships between the bore or inner diameter of the suction catheter and the force of the suction source can be employed/engineered as desired or needed in order to provide sufficiently efficient scavenging of the wearer's expired air from the mask area to prevent fogging. The construction of the mask is important, comprising variables of mask design (including effective area for evacuation of air upon expiration), permeance of mask materials, placement of the end of the catheter within the mask and internal diameter of the catheter. Too great a suction force—i.e., too large a tubing—however, can create collapse of the mask, can cause facial skin to be drawn into the tubing end, or create irritating noise to the wearer and others. The embodiments described would allow a surgeon or other user to apply the mask quickly and easily, providing a consistent and reliably snug seal about the face for mutual protection of the wearer and patient or other work space materials, eliminating the fogging of eyeglasses and microscopes, and providing cool, fresh breathing air to the space area between the mask and the wearer's face for a more pleasant work environment and lowered fatigue.

A preferred way of practicing this invention is to incorporate a simple suction catheter of approximately 8–20 French diameter (about 1.6–4.0 mm i.d.) and 20–30" (51–76 cm) in overall length. A preferred length (about 40" or 102 cm) would put the end of the tubing about waist level with the tubing passing over the shoulder of the wearer. For operating room use, the tubing is preferably incorporated into the manufacture of a mask design like that manufactured by Tecnol Corporation of Dallas, Tex. U.S.A. (Tecnol PCM2000, #47118-010, note FIG. 11, Mask "O"). Other disposable mask designs with elastic straps or other mechanism to afford a tighter seal between the wearer's face and the mask may also be used, such as Tecnol's PFR95 (order #47119-170, note FIG. 11, Mask "C") mask. The tubing can be inserted in the mask using a grommet (FIG. 2) or by using a sleeve (FIG. 3).

It is a purpose of the invention herein to augment the permeable face of the mask to remove exhaled air of the wearer from the zone between the mask and the wearer's face by a combination of the exhaled air leaving through the mask and aspiration of the air from the mask zone through the suction source. Concurrently, air is returned to the zone by inhalation of the wearer and by replenishment through the mask of the aspirated air. By replenishing the space between the mask and the wearer's face with air from the mask surface rather than concentrating the flow through an inlet orifice, the flow becomes more uniform and at a slower pace, avoiding distracting noise or velocity disturbances. Thus, a comfort level of wear that not only minimizes the fogging of any eyewear, but removes warm, moist exhaled air from the facial zone, is a function of the permeability of the mask material and the aspiration level via the vacuum source.

Hospital aspirating systems have various vacuum levels, depending on the location and equipment used. In the United States, such systems usually have a vacuum level of 15–20 inches Hg., although some systems may be as low as 12 inches Hg and others 22 inches Hg. Thus, the aspiration capability of the vacuum source in a hospital surrounding may be considered a function of the tubing size and length of tubing used to connect from the wearer to the vacuum source. A normal breath contains about 300–350 $cm^3$ air. One breathes—inhales and exhales—about every 4–7 seconds. The aspirating force from the vacuum system will be constant, although the inhalation/exhalation cycle is periodic. A vacuum system that removes air from the zone between the mask and the wearer's face during the breath cycle is sufficient for removal of the warm, moisture-laden air exhaled by the wearer and the prevention of fogging of optical devices worn. It has surprisingly been found that vacuum tubing of at least about 8 French (1.6 mm) and preferably about 14 French (2.8 mm) can sufficiently aspirate the warm, moisture-laden air from a conventional pervious mask in service at this vacuum level. Use of a conventional mask having a relatively large pervious surface area provides ample clean dry air without creating substantial concentrated flows across the medial facial area.

U.S. Pat. No. 5,322,061 to Brunson (the disclosure of which is incorporated fully herein) describes a preferred mask of the type utilized in this invention. The mask therein contains multiple layers of mask material, about 250 $cm^2$ surface area being pervious to gases with approximately $1\mu$ particle size filtration capability. With a mean pressure differential across the mask surface area of about 1.25 mm $H_2O$, the mask has excellent breathability characteristics in itself. Combined according to the present invention, however, with an aspirating tubing of about 2 mm internal diameter connected to a 15–20 inches Hg vacuum source, the mask provides excellent eyeglass fog resistant qualities and provides a cool, dry air to the user, resulting in substantial increases in user comfort.

In the embodiment of FIG. 1, a device 43, such as a needle valve or other flow-varying means is adjacent to the first end 33 of the catheter tube 31 for adjusting a flow rate through the catheter tube 31 caused by the suction source 37. The flow-varying means 43 may be in the form of, for example, a closable opening 45 in line with the catheter such that the suction source 37 tends to draw more air through the opening, when opened, than through the second end 35 of the catheter. If desired, multiple flow rate adjusting devices 43 may be provided in series with one another.

Figure 2:
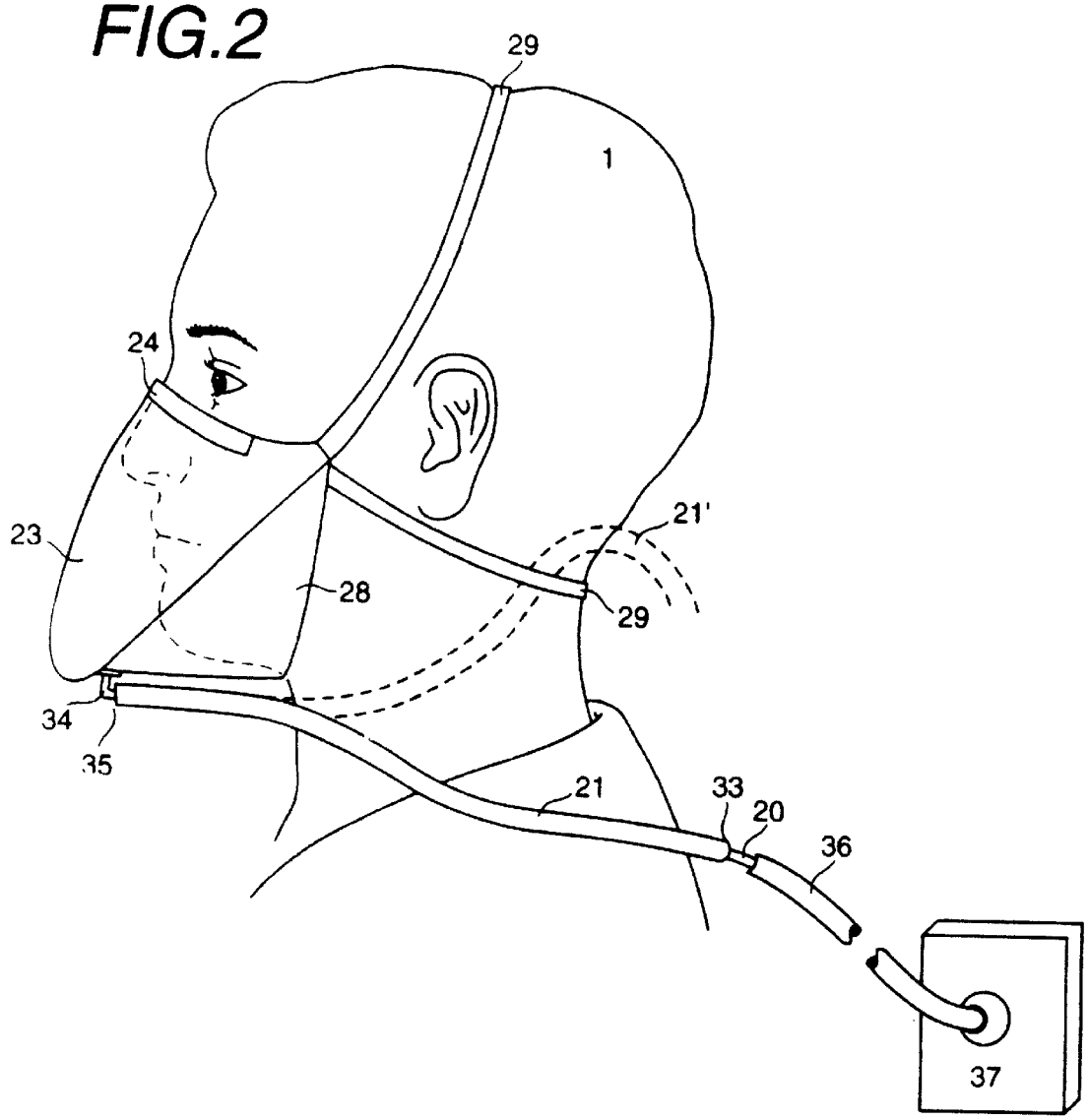
FIG. 2 is a side view of another embodiment.
Figure 3:
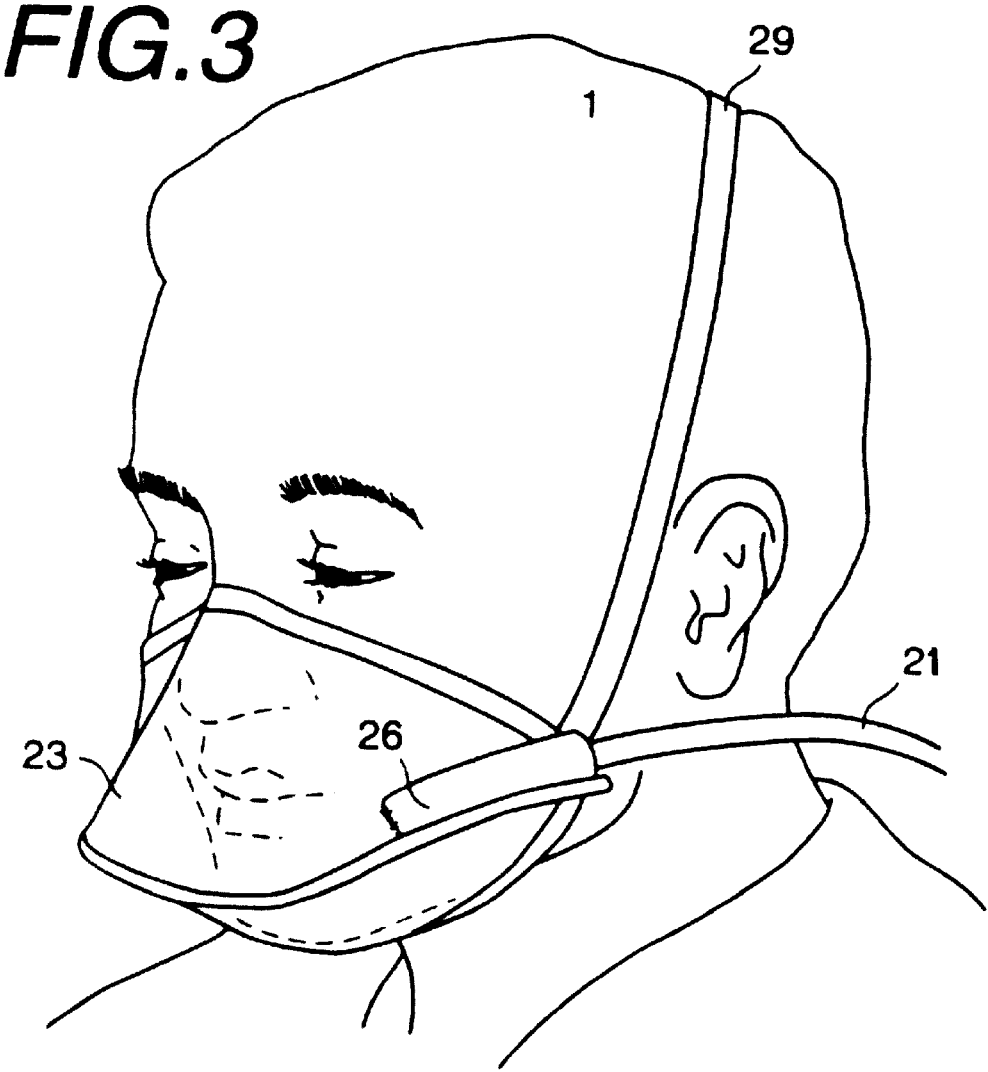
FIG. 3 is a third embodiment utilizing a mask of preferred construction.

In the preferred embodiment of FIG. 2, a mask design disclosed in U.S. Pat. No. D347,713 to Brunson has been adapted. Such a mask is further described in U.S. Pat. No. 5,322,061 to Brunson. U.S. Pat. Nos. 5,322,061 and D347, 713 to Brunson (Mask "C", FIG. 11B) are incorporated by reference. The use is made of a malleable strip 24 to mold the mask to the face of the wearer. Mask 23 is shown on a wearer 1 held in place by ties 29, although elastic bands are most preferable. A tubing 21 of approximately ⅛" (3.175 mm) internal diameter and ³⁄₁₆" (4.76 mm) external diameter of appropriate plastic material, including polyurethane, nylon and polyethylene, is of length to enable the user to move freely at his work station while the other end is connected to a vacuum source 37. Tubing of 14–18 French (2.8–3.6 mm) internal and diameter are most suitable (FIG. 11A). Alternatively, and as shown, the tubing 21 may be of a short length 10"–24" (25.4–60 cm), sufficient to attach to a first end 33 via coupling 20 to a second tubing 36 which is connected to the vacuum source 37.

The embodiment of FIG. 3 shows the Tecnol PFR95 mask 23 adapted to accommodate the tubing 21 within a sleeve formed in the mask. The sleeve 26, depicted in FIGS. 6 and 6A, is formed as upper mask section 36 is joined together at seam 22. In the use of thermoplastic materials, the seam can be through known heat seal techniques. For other materials the seam can be made through known stitching techniques.

A seam 22 is formed around the outer edge of the top and bottom sections 28 and 30 when laid together. Seam 32 is spaced sufficiently from seam 22 for tubing 21 to fit tightly in the sleeve thus formed.

Figure 4:
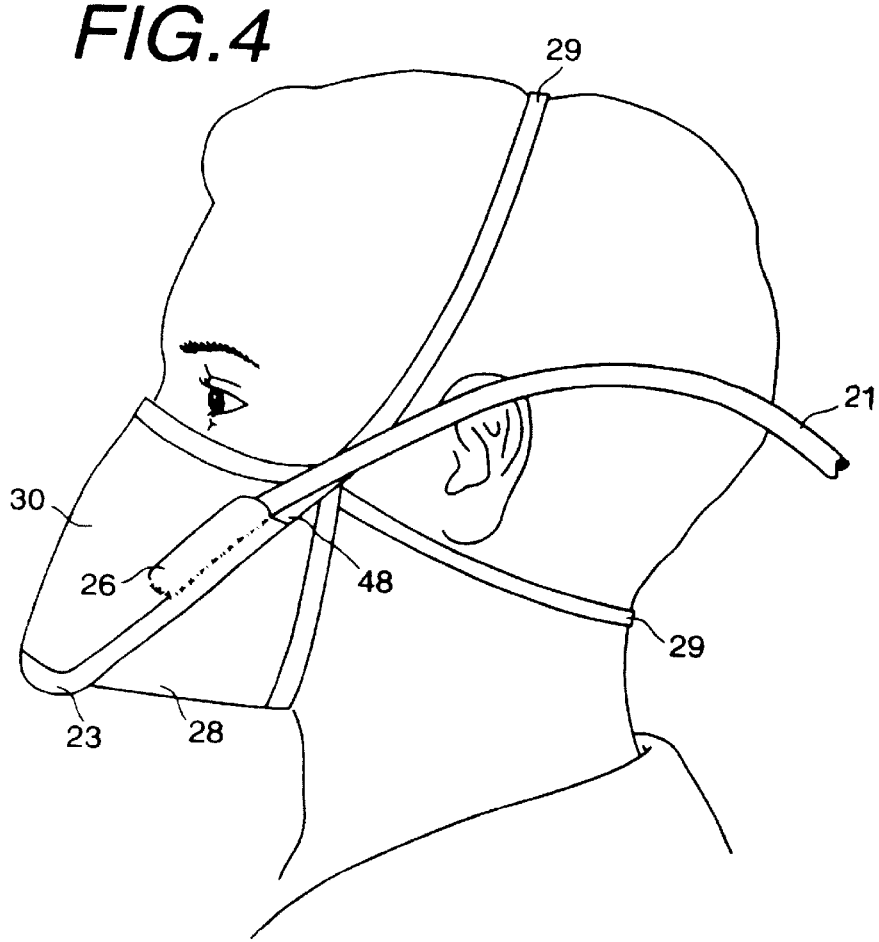
FIG. 4 and FIG. 5 are alternative constructions of the mask and tube.
Figure 5:
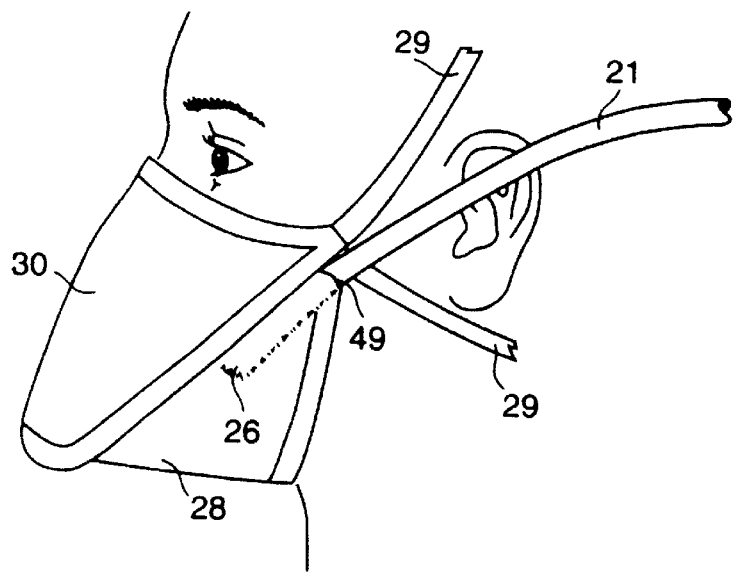

In FIGS. 4 and 5, tubing 21 is inserted through openings 48 in the top section 30 of the mask 23 or through opening 49 in the bottom section 28. A sleeve 26 can be bonded/stitched into the seam of the mask by forming a fold of material and inserting it as it is being manufactured. The sleeve 26 will accommodate tubing 21 when placed through either hole 48 or 49. holding the tubing in place. The tubing tip 40 is secured in the inner section of the sleeve 26, as shown in FIG. 7. While placement of the end 35 is not critical, it should be placed to draw exhaled air from the nose/mouth area with minimum constriction. As shown in FIGS. 8 and 8A, as well as in FIG. 7, the tip of the tubing may be angled (40), have holes 42 or a slit 44 formed to dissipate the localization of the suction which otherwise may cause the tubing end to be pulled into facial tissue of the wearer or alternatively concentrate aspiration through the mask material by the suction effect of the aspirating air.

End 35 of tubing 21 may be connected to an ell tubing adapter 34 to the underside of section 28 of the mask 23. As shown in FIG. 10, the ell tubing adapter projection 17 extends through opening 19 in the mask section 26. A friction washer 38 slips over the projection 17, holding the adapter 34 in place on the mask section 26 against adapter flange 18, thereby sealing the opening 19. The advantage of the ell adapter is that it directs the tubing away from the operating area of the wearer, rather than having it hang downwardly into that area. Tubing 21 may be attached by clip means to the wearer's clothing, as shown in FIG. 1 or allowed to hang loosely depending on the wearer's desires. Alternatively and as shown in imaginary lines, the tubing 21 may be captured by a tie 29 to prevent excessive pulling on the face of the mask. FIG. 9 depicts a flanged nipple adapter 46 for accepting a tubing end 35. A similar adapter is described in U.S. Pat. No. 3,130,722 to Dempsey, et al. Such an adapter may be used in place of the ell adapter 34. Either adapter, the friction washer, or both may be of metal or plastic, as preferred.

Air flow through the mask created by the aspiration of air through tubing 21 not only helps prevent fogging of the glasses but also makes the wearing of this mask more comfortable. By drawing in dry air with the removal of warm, moist exhaled air, the zone of space between the mask and the face can be kept relatively comfortable. The intake of this dry air and expelled moisture helps to maintain the dryness of the mask material, which otherwise will become saturated with the exhaled moisture. The surface area of a mask may be 200–300 $cm^2$, while the effective surface area will be somewhat less—generally 40–100 $cm^2$—due to mask construction and the wearer's facial configuration. Various levels of unit pressure differential across the mask will be noted depending on the mask makeup.

As has been noted, normal human breathing ranges between 4–7 seconds, inhaling and exhaling 300–350 $cm^3$ air with each breath. Normal breathing pressure is about 1 inch or 25.4 mm $H_2O$. At normal breathing, a wearer would exert just under 2 pounds of force on a 300 $cm^2$ mask having a pressure differential of 1 mm $H_2O$ across the mask. At a higher differential of 4 mm $H_2O$, the force would be about 8 pounds. Such forces can cause masks to deform and/or become uncomfortable. It is desired to keep the additional force of the suction catheter aspiration within limits so that the two forces—inhalation by the wearer and the aspiration of the tubing—do not override the mask structural characteristics.

Thus, it has been found that the aspirative force must be confined within limits for best results. By utilizing the air dissipating effect of the mask 23 and aspirating effect of tubing 21, a combination of elements can be determined to provide protection for the wearer, the operation's environment, as well as provide comfort and clarity of vision.

For purposes of this invention, masks having a pressure differential ($\Delta p$) below 0.6 mm $H_2O$ will likely have little more than protection for macro sized particles. Aspiration of such masks likely will be at the contact point of opening of the tube with the mask. The preferred range of mask performance level for this invention involves permeable materials between about 0.6 and 10 mm $H_2O$ $\Delta p$ at conventional breathing conditions.

The space or aspiration zone between the mask and face of the wearer depends upon the construction of the mask and wearer's facial configuration. The space typically comprises 15–40 $cm^3$ centered around the nose and mouth. If the mask zone is 30 $cm^3$, 270 $cm^3$ of a normal breath could be exhaled through the mask of ordinary permeability. This warm, humid air could rise and affect the wearer's glasses. Thus, the removal by the suction tube—having normally a 15–20 inches Hg vacuum in the United States—of about 300 $cm^3$/sec. will remove substantially all the expired breath, substantially eliminating moisture that would, without aspiration, be captured by the mask material, and provide a zone of comfort for the wearer. The diameter of the catheter, with a given range of vacuum, can be considered a function of the air permeance (or pressure drop) across the mask material. For increased pressure drop across the material, the diameter of the catheter tubing will increase to maintain sufficient aspiration. As the effective area of the mask is reduced by design or facial configuration, the tubing size will also increase. In U.S. hospitals where there is as much as 21–23 inches Hg. vacuum supplied in hospital operating rooms, even a gas impermeable mask may not require more than a 20 French diameter (4.0 mm), but the mask may not be able to withstand the aspirative forces. The comfort/no fogging zone can be understood by reference to FIGS. 11–11B. The comfort zone of the present invention can be provided by a mask construction within the boundaries of a mask permeance about 350 and 4600 $m^{-6}$/Pa.S about 150 to 600 $cm^3$/sec. suction tubing flow rate.

EXAMPLE 1

A mask as described in U.S. Pat. No. 5,322,061 to Brunson and a tubing 21 of about 2.8 mm i.d. and 24 inches in length is placed on a wearer with the mask end of the tubing in communication with the space formed by the mask and face around the nose of the wearer. The wearer performs an operation under conventional operating room conditions. The operation lasts 1 hour. During that hour, the other end of tubing 21 is attached to approximately 16 feet of tubing 36 of 7 mm internal bore, the other end of which is connected to a Guardian liquid collection canister assembly which, in turn, is connected to a wall vacuum outlet. The vacuum measurement at the wall is 23 inches Hg. A liquid catch jar in the canister assembly is upstream of the wall outlet, followed by a regulator supplying a set vacuum of 20 inches Hg to tubing 36. At the beginning of the operation procedure, the catch jar is empty. After the 1 hour period in which the tubing 36 has been connected to the mask/tubing connection of this invention and worn, 20 cc of accumulated condensation from the wearer's breath is measured in the catch jar.

EXAMPLE 2

This example shows the effective pressure drop due to tubing. At the wall of a conventional vacuum source in a North Texas hospital, the measured air evacuation rate was at 1400 cm$^3$sec. This connection outlet is joined by a standard plastic male-male connector with two sets of tubing each length being 12 feet (3.65 m) long with an internal diameter of 4.8 mm, the tubing purchased from Davol Company, catalog number 3656. A single Guardian canister assembly was arranged between the wall source and the patient, comprising one 3,000 cc Guardian canister. At the end of the 24 feet of Davol 3656 tubing, a 24" (60.96 cm) length tubing is attached with a tubing diameter of 8 French (1.6 mm). The flow rate in the 8 French catheter tubing was measured as 145 cm$^3$/sec. The 1.6 mm tubing was considered the minimum size for comfort of use.

EXAMPLE 3

The 24 inch (60.96 cm) section of flexible plastic tubing in Example 2 was replaced with a 2.0 mm i.d. tubing (10 French)section of similar 24 inch length. A 21,000 cc bag was filled with air, connected to the tubing and the air evacuated. The process was repeated three times, timing each time the period of evacuation. The average time of air removal from the bag was 105 seconds. The effective air removal from the bag , then, was 280 cc/sec. This demonstrates the effective air removal by a 2.0 mm tubing in the setup described is 280 cc/sec.

EXAMPLE 4

The 24" (60.96 cm) section in Example 3 was replaced with 2.8 mm i.d. tubing (14 French) and similar testing was performed with the 21,000 cc bag. The average evacuation time was 50 seconds. The effective air removal was then 420 cc/sec. In use tests, the 2.8 mm tubing was the preferred for comfort of use.

EXAMPLE 5

The 24" (60.96 cm) section in Example 4 was replaced with a 3.7 mm i.d. tubing (18 French) and similar testing was performed with the 21,000 cc bag. The average evacuation time was 37.5 seconds; the effective air removal was 560 cc/sec.

The results of Examples 1–5 show that with a conventional vacuum force of 22 inches Hg at the wall in a surgical operating room in Texarkana, Tex., USA, the flow rate of air at the wall source after a conventional canister (Baxter Healthcare, Canister No. 64-3480A) and after 24' of connector tubing terminated by various diameter catheters was as follows:

CHART 1

|  | Internal Diameter | Flow cc/sec |
| --- | --- | --- |
| At wall |  | 1400 |
| Wall side of canister to valve | 4' of 7 mm tubing | 1400 |
| Valve to canister | 1' of 10 mm tubing | 1000 |
| End of 24' connector rubing from canister | 4.8 mm | 560 |
| plus 18 French catheter, 2' long | 3.6 mm | 560 |
| plus 14 French catheter, 2' long | 2.8 mm | 420 |
| plus 10 French catheter, 2' long | 2.0 mm | 200 |
| plus 8 French catheter, 2' long | 1.6 mm | 145 |
| plus 5 French catheter, 2' long | 1.0 mm | 80 |

Of course, the flow rate will vary not only with respect to the vacuum force at the source, line drop, diameter of connecting tubing, but the length of catheter tubing to the claimed device, and finally, catheter internal diameter.

EXAMPLE 6

Applicant tested a number of commercially available masks in order to determine the comfort zone using the invention herein and the masks. The style and fit of each mask was noted, and the sense of warmth about the face of the wearer was assessed after several breaths. The open end of the large, 4.8 mm internal diameter connector tubing was placed into the space between the mask and face of the wearer, with the wearer sealing the opening about the entrance of the tubing with the fingers. An assessment was made of the degree to which the sense of warmth was diminished, creating greater comfort. Also noted was whether the suction tended to collapse the mask. No collapsing occurred with any mask until the breathable mask surface was restricted by applying non-porous tape. After testing the effect of the open connector tubing, the various French size catheter tubings in diminishing sizes were connected and the observations as to degree of comfort was assessed. The results of the testing are set out in FIGS. 11, 11A, 11B and 11B(a).

Reference is made to FIGS. 11, 11A, 11B and 11B(a) which are charts of mask parameters and an evaluation of the comfort levels obtained by the invention herein. A series of masks A–EE were evaluated for the invention. The description of the masks is set out in FIG. 11B and 11B(a). The air permeance and potential flow through the evaluated masks are set out in FIG. 11. The mask construction (type) and ratings with and without aspiration are contained in FIG. 11A.

Under the column labeled "Breathability" in FIG. 11A, various masks are rated between 1 and 3—1 being least breathable to the wearer; 2 being medium, and 3 being most breathable. The "comfort level" of the masks with a suction catheter tube placed in the area of the nose and mouth of wearer was determined and is set forth in the so-labeled columns. The "at rest" column is the comfort level of the mask without aspiration. The column labeled "Type" refers to the style of the mask, as follows: C=Contour; Cn=Cone; D=Duckbill; Sh=Shield; St-Elastic Straps; T=Tie Strands; L=Ear Loops. All cone masks have elastic straps.

The air permeance of the mask material is determined using a Gurley porosimeter (manufactured by the Teledyne- Gurley Company located in Troy, N.Y.) with a 5 ounce (0.3 KPa) weight on 100 milliliters air through an orifice 0.645 cm² in area in accordance with International Standards Organization (ISO) No. 5636/5 test procedure. The air permeance P(m⁻⁶\Pa.S) is equal to 100÷(645×Δp×t). Δp is 0.3 KPa; t equals the number of seconds required to pass 100 milliliters air through the 0.645 cm² orifice and mask material. The air permeance of tested masks are set out in FIG. 11A.

$$P = \frac{100 \, ml}{(1000)(\Delta p)(t)} = (1) \quad (1)$$

In considering a flat mask material, the flux of gas can be determined from D'Arcy's Law to be $$N_0 = \frac{\kappa \Delta p^2 A_0}{2\mu RT\lambda} g \text{ moles/sec}$$

where κ=permeability of the material; μ=gas viscosity; R=gas constant; T=temp; λ=distance between samplings; Δp=driving force; A0=area.

In testing with a Gurley porosimeter and using a 5 ounce (0.3 KPa) weight on a cylinder volume of 100 milliliters passing through a material area (A0) of 0.645 cm², the data of FIG. 11 was arrived at using the following equations:

(2) Δp=0.3 KPa·1 mm H₂O/9.8 Pa=30.61 mm H₂O;

(3) N0 =(100 ml)(1 g mole)÷(30.61)²t=(2) g moles/sec;

$$\frac{\kappa}{\mu RT\lambda}(2 N_0) \div (30.61)^2 * (0.645) = (3). \quad (4)$$

For a mask having a 250 cm² surface and a pressure drop of 2 mm H₂O across the face, one obtains $$250 \, cm^2 \times \frac{\kappa}{\mu RT\lambda} \times 2 \, mm H_2O \times 22,400 \text{ moles air/cm}^3 = \quad (5)$$

$$(4) \, cm^3/sec.$$

The "breathability" of each mask was assessed by placing the surface tight against the wearer's open mouth and inhaling and exhaling several times. Masks were compared in pairs, and a distinct ranking was established in masks A–G, from the most breathable (1) to least breathable (7). This ranking is indicated by an asterisk (*). Masks H–EE were evaluated on a scale of "Breathability" between 1 and 3, with 1 being least breathable, 2 being medium and 3 being most breathable.

The comfort level of the masks with various suction catheters placed in the nasal and mouth area was established and are set forth in the labeled columns of FIG. 11. The base line comfort level without aspiration was noted. The evaluation criteria (FIG. 11A) were: 1—hotter than average; 2—average comfort; 3—cooler than average.

Tubing sizes of 5 French (1.0 mm i.d.), 8 French (1.6 mm i.d.), 10 French (2.0 mm i.d.), 14 French (2.8 mm i.d.), and 18 French (3.6 mm i.d.) were evaluated with a vacuum source of 20 inches mercury. The following rating scale was used:

0 No perceptible difference noted with or without aspiration

1 Barely perceptible differences with aspiration
2 Improvement with aspiration
3 Almost full benefit of aspiration
4 Full air conditioning benefit The comfort zone according to the invention is readily apparent from FIG. 11C. The aspiration rate is compared with air permeance values of masks A–EE as set out in FIG. 11A. For purposes of emphasis, air permeance values higher than 2000 are not depicted. FIG. 11C is divided into zones— 1) ineffective; 2) unpredictable; 3) marginal comfort; 4) relative comfort; and 5) full comfort. See Chart 1 for aspiration rates corresponding to the tubing sizes set out in FIG. 11A.

For the masks tested (A–EE) those having comfort levels of 0 or 1 were considered ineffective in removing the warm, moist air from the area between the mask and the face of the wearer. These mask assemblies represent the "Ineffective Zone" as shown. It should be recognized that masks with permeance values greater than 2000 can be aspirated satisfactorily at these rates.

At levels of aspiration greater than 80 cc/sec but below 145 cc/sec. There is a zone where the mask construction versus air permeance and aspiration rate was indeterminate. This zone has been labeled "unpredictable" in FIG. 11C. Mask "J", for example, has a comfort level of 3 at 150 cc/sec. Masks "P"–"S", on the other hand, have merely a comfort level of 1.

The "Marginal Comfort" zone is shown beginning at about the 1200 air permeance level for an aspirating rate of 200 cc/sec and contains no aspirating comfort level ratings less than 2 or greater than 3. Some improvement was shown in comfort level for masks in this zone.

The "Relative Comfort" zone comprises masks predominantly having ratings of 2 and 3 and air permeance values of 1200 or higher. Mask "W" was the only mask in this description falling in the "Marginal" ranking with a "1" rating.

Full comfort is realized with ratings of "4". At this level of aspiration and air permeance the full air conditioning benefit of the invention is achieved. The latter three comfort zones are considered within the scope of the invention. Depending on the mask construction, the aspirating zone for 80–145 cc/sec will satisfy the criteria of the invention that the confort level be at least 2.

Applicant then took the "tightest"—i.e., least comfortable—mask, C, and applied strips of adhesive tape and tested at intervals until the entire mask was occluded. No differences were noted until the final stage, at which point the mask (simulating an impervious mask) did collapse with the 14 French and larger catheters; the smaller size catheters neither collapsed the mask nor effected any appreciable difference in the comfort level. At the fully occluded level, however, air entered and escaped around the malleable portion contoured to the bridge of the wearer's nose. When that seal was manually maintained by the wearer, the wearer could not breathe in, and expired air escaped around other edges.

Experimental results show that with minor variations, for all masks in this breathability range, 14 French and larger tubings created good comfort levels, with essentially complete removal of warm, humid breath. Tubings from 8–14 French had almost invariably improved comfort levels. Smaller tubings had marginal or no effects. It had been expected that the smaller tubings might be sufficient with those mask designs that are better contoured to the wearer's face or that allow more surface area in the vicinity of the mouth and nose and therefore have a larger air volume in the mask-face space, or zone. However, this was not appreciably the case, nor did there appear to be any appreciable differences in results of comfort among the range of mask permeances and breatheabilities tested, which may indicate that they are all fairly close together on the air permeance scale.

Initial Theoretical Engineering Calculations on Catheter Sizing on Line Loss of Hose to Catheter To determine the influence of the connecting tubes on the functioning of a surgeons mask, Applicant started with a mechanical energy balance because in considering a gas (small density), kinetic and potential energies may be neglected and the following simplified balanced equation be written:

$$\int_{P_1}^{P_2} \frac{dp}{\rho} = E_f = \text{losses due to friction} \qquad (6)$$

where $\rho$ equals the density of ideal gas.

For isothermal flow of an ideal gas with $P_{a/m} \gg x_0$, this equation is to an excellent approximation $$\ln\left(\frac{RT[P_{atm} - X_0]}{M_w[P_{atm} - X]}\right) + E_f = 0 \qquad (7)$$

From the book *Transport Phenomena* by Bird Steward and Lightfoot, we find $$E_f = \langle v^2 \rangle \frac{L}{r_s} f \qquad (8)$$

where $r_s$=radius of the connecting tube, L is the length of the tube, $\langle v \rangle$ is the average velocity of gas in the connecting tube and f is known as the friction factor. For a restricted range of Reynolds numbers, the friction factor may be calculated using the Blasius equation:

$$f = \frac{0.0791}{(RE)^{1/4}} \text{ for } 2{,}100 < RE < 1 \times 10^5 \qquad (9)$$

Each time this equation is used, it must be ensured that the Reynolds number is in the proper range. Since both x and $x^0$ are very small as compared to $P_{a/m}$, the mechanical energy balance may be further simplified to the following:

$$\frac{RT}{M_w} \frac{[X - X_0]}{P_{atm}} = \frac{1}{2} \langle v \rangle^2 \frac{L}{r_1} f \qquad (10)$$

The aspiration rate is V (cm³/sec) and therefore $$\langle v \rangle = V/\pi r_1^2$$

The Reynolds' number is by definition $$RE = \frac{2\rho \langle v \rangle r_1}{\mu} = \frac{2PM_w}{\mu RT} \frac{V}{\pi r_1} = $$
$$\frac{2(30)(1\text{atm})}{(1.813 \times 10^4)(82.05)(300)} \frac{V}{\pi r_1} = 4.196 \frac{V}{r_1} \text{ whence} \qquad (11)$$

$$RE^{1/4} = 1.431\left(\frac{V}{r_1}\right)^{1/4} \qquad (12)$$

therefore applying the Blasius Equation.

$$f = \frac{0.0781}{RE^{1/4}} = 5.46 \times 10^{-2} \left(\frac{r_1}{v}\right)^{1/4} \qquad (13)$$

In terms of the friction-factor, the friction losses are given by $$E_f = \langle v^2 \rangle \frac{L}{r_1} f = \frac{V^2}{\pi^2 r_1^4} \frac{L}{r_1} f = 5.52 \times 10^{-3} \frac{LV^{1.75}}{r_1^{4.75}} \qquad (14)$$

The final expression for the flow in the tube is therefore $$\frac{[x - x_0]}{[P_{atm}]} = 6.5199 \times 10^{-12} \frac{LV^{1.75}}{r_1^{4.75}} \qquad (15)$$

if $x_o$ and xo are expressed in terms of mm H$_2$0, ten the final working equation is $$x_0 - x = 6.736 \times 10^{-8} \frac{LV^{1.75}}{r_1^{4.75}} \qquad (16)$$

This equation must be coupled wit the equation giving the aspiration rate across the mask in terms of the vacuum pressure at the mask, x mm H$_2$O, and the vacuum pressure at the source, $x_o$. Thus, we have a complete relationship that must be solved as a unit. This calculation illustrates that for a great majority of the length of the hose from the wall source to the catheter, the internal diameter of the hose leading to the catheter should not be substantially smaller than 5 mm.

In many discussions in the prior art, the artisans state that fogging is caused by the warm, humid air escaping around the edges of the mask, particularly the upper edge. This is their basis for all these plastic strips, slits, foam pad barriers, and the like, designed to deflect the warrn air elsewhere. With these easy-breathing masks, it is believed that the warn air that passes through the mask material is sufficient to rise up and cause fogging of glasses. This is likely the explanation for the failure of all these prior art designs to solve the fogging problem. Clearly, then, it would seem desirable to aspirate essentially all of the expired breath, as the 14 French and larger tubings seem to do, and not just the 10–20% that remains in the mask-face zone, as previously considered sufficient.

It has also been found that the mask of the invention as described herein can be used as a breathing aid for patients, permitting the use of a low cost, disposable mask of permeable material for supplementing the breathing of a patient by supplying a gas such as clean, dry air or oxygen to the wearer. As a patient breathing aid, the mask of the invention is fitted over the mouth and nose of the patient. A volumetric zone or space is formed between the mask and the face of the wearer/patient. A determined amount of gas is fed to the mask via flexible plastic tubing connected to the mask from a source of the gas.

A volume control means may be interjected into the tubing line and the source to adjust the flow of the gas to the conditions required by the wearer/patient and sufficiently expel the warn, moisture and carbon dioxide laden exhaled air from the patient through the mask material. When tested with the volume control valve open, however, the conditions inside the mask were comfortable to the wearer, as excess air/oxygen flowed through the mask. Each patient will have a different level of flow need. Medication may also be periodically be administered through the system disclosed herein, with the medication not directly inhaled entering the mask and providing extended use as the patient inhales through the mask material. It is also considered a part of the invention herein to interrupt the flow and volume of gas to the mask as determined to augment the patient's breathing and/or to adjust the medication being supplied to the patient.

For use as a positive-pressure oxygen, air, or other gas delivery mask, especially for use by patients with or at risk for communicable or opportunistic illnesses spread by aerosol droplets, the preferred embodiment is a duckbill style mask like the Tecnol Mask "C" (PFR95) or Mask "M", depending upon the degree of filtration desired. For use by patients in whom spread of respiratory-borne illness is not a concern, a mask with a greater permeability such as Mask "O" might be preferred if it is less expensive to produce.

Figure 12:
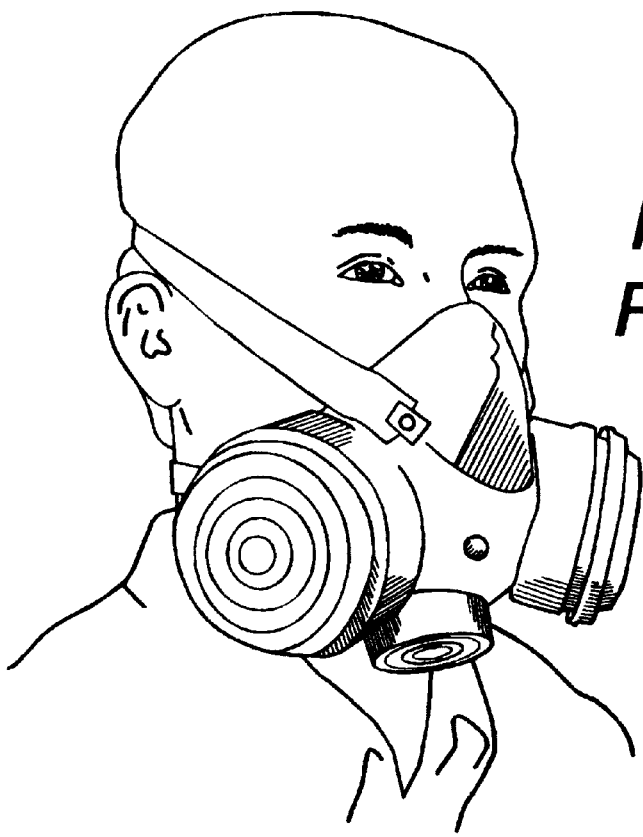
FIGS. 12 and 12A are examples of prior art respirator type masks.
Figure 13:
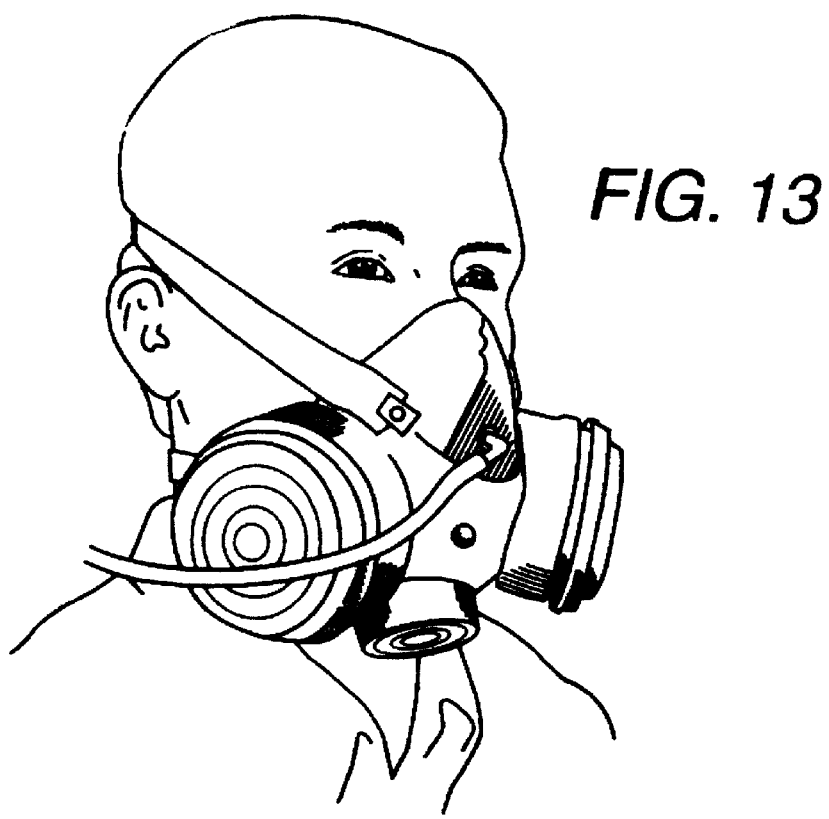
FIGS. 13 and 13A are prior art respirator type masks having connecting tubing according to the invention herein.

The positive flow mask may also be used in conjunction with industrial applications involving heavy dust particles. FIGS. 12 and 13 are examples of prior art devices used in heavy industrial applications such as painting in close areas. Such devices are expensive initially and utilize filter cartridges that must be replaced often. Devices of the invention as shown in FIG. 3, when used with a positive clean, dry air supply source will supply a comfort zone of usage for the wearer not provided by the prior art devices.

For this industrial usage, it is preferable to use a mask of pervious material that has the back face or inner surface distant from the nasal and mouth area of the user. This inhibits the concentration of particulate materials in the ambient atmosphere from accumulating on the outer surface of the mask in those two areas from the inhalation of the wearer. Focusing the end of the tubing 21 in the nasal and mouth area aids in preventing the concentration of particulate materials, as the wearer inhales predominately air from the positive supply source. The amount of air utilized in such industrial applications will be greater than the patient aid system in that the activity of the wearer will place greater demands on the air supply. Preferably, the majority of the air inhaled by the wearer will come from the air supply. Use of a masked device as disclosed, however, permits the wearer to determine how much air will be breathed through the mask and how much air will come from the air supply source. The proportion will be a function of the level of particulate materials in the air.

For use as a respirator for painters, the preferred embodiment is a duckbill style mask like the Tecnol Mask "N" with a clear plastic shield to prevent paint splashes from getting into the wearer's eyes. This mask style also has a foam strip along the inner upper aspect of the face shield which would serve to prevent paint spray and droplets from gravitating down from above between the eye shield and the eyes.

Figure 12A:
Figure 13A:
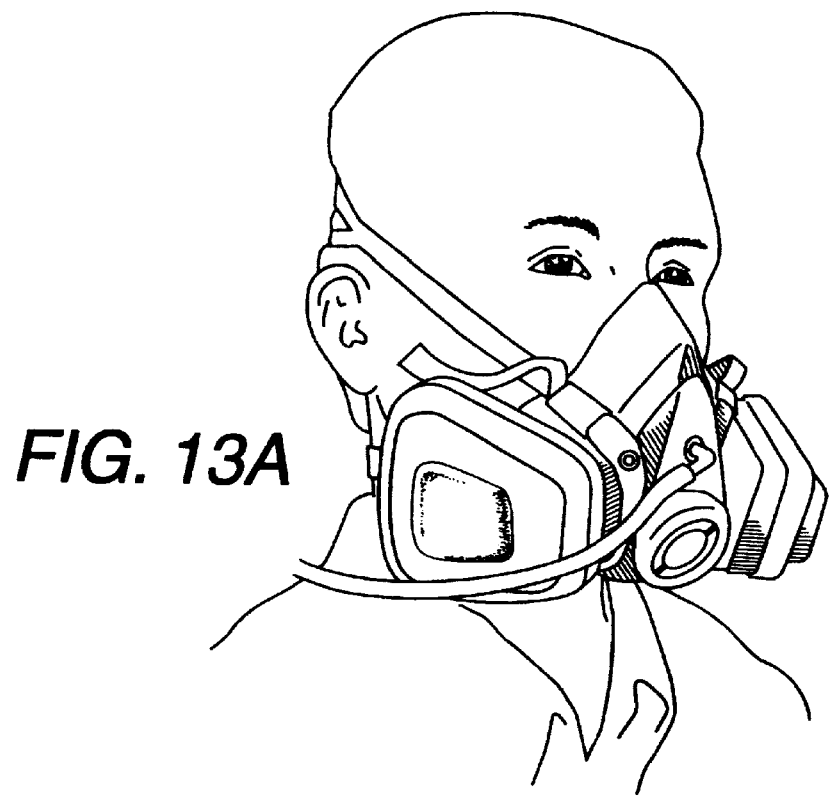

It is also considered herein that prior art respirator masks may be conveniently fitted with an air source as described herein. FIGS. 12 and 12A represent masks of the prior art Binks Model 48970 (FIG. 12) and 3M No. 5200 (FIG. 12A). FIGS. 13 and 13A show the masks retrofitted with tubing ell adapter 34 and 21, which, in turn, is connected to a positive air/gas supply not shown.

It will be apparent to one of ordinary skill in the art that for a given hospital, by measuring the standard vacuum rate at the wall and by choosing a desired mask for the type of surgical or dental work to be performed, that a most-desired catheter tubing may be selected with little experimentation.

It will be appreciated that, because the above-described materials are relatively inexpensive and easily assembled, the disposable mask and catheter tube 21 according to the present invention can be constructed at minimal cost, yet provides greatly improved comfort for wearers of masks, particularly surgical-type masks. Also, the mask is readily removable without injury to the wearing face. Because of the ready availability of suction sources in operating-room environments, the disposable mask and catheter tube 21 has particular application in the context of surgical masks; however, the disposable mask and catheter tube can, of course, be used in any environment where wearing of a mask is necessary and a suction source is available.

It is, of course, possible to embody the invention in specific forms other than those described above without departing from the spirit of the present invention. The embodiments shown are merely illustrative and should not be considered restrictive in any way. The scope of the present invention is given in the appended claims, rather than the preceding description, and all variations and equivalents which fall within the range of the claims are intended to be embraced therein.

What is claimed is:

1. A disposable mask and suction catheter, comprising: a disposable pervious mask having a front side and a back side, the back side being disposed in contact with a user's face during use, allowing a user to breathe through the mask during an operation; and a length of relatively inexpensive lightweight suction catheter tubing having a first end and a second end, the first end adapted to be connected to an available hospital operating room suction source for removing exhaled air, and the second end being in communication with the back side of the mask to receive exhaled air from a user.

2. The disposable mask and suction catheter as set forth in claim 1, further comprising means for removably attaching the catheter tubing to a user's clothing.

3. The disposable mask and suction catheter as set forth in claim 2, wherein the removable attaching means includes a clip.

4. The disposable mask and suction catheter as set forth in claim 1, wherein the second end of the catheter tubing is fixedly attached to the back side of the mask.

5. The disposable mask and suction catheter as set forth in claim 4, wherein the second end of the catheter tubing is fixedly attached to the back side of the mask by an adhesive tape.

6. The disposable mask and suction catheter as set forth in claim 1, further comprising flow rate adjusting means, attached to the catheter tubing, for adjusting a flow rate caused by the suction source.

7. The disposable mask and suction catheter as set forth in claim 6, wherein the flow rate adjusting means includes an openable and closable opening in line with the catheter tubing such that the suction source tends to draw more air through the opening, when opened, than through the second end of the catheter tubing.

8. The disposable mask and suction catheter as set forth in claim 6, wherein the flow rate adjusting means includes a valve.

9. The disposable mask and suction catheter as set forth in claim 7, wherein the flow rate adjusting means includes a needle valve.

10. The disposable mask and suction catheter of claim 1, wherein the catheter tube is a suction catheter of about 14 French.

11. A method of removal of stale, humid air from a surgical mask in use as in claim 1, comprising the attachment of the first end of the suction catheter tubing to an available operating room suction source.

12. A method of removal of exhaled air from an area between a disposable mask and the face of the mask wearer, said mask having a suction catheter tube of about 14 French diameter attached at a second end to the mask, said second end of the catheter tube in communication with a backside of the mask for exhaust of said exhaled air, including attaching the first end of said catheter tube to an available, non-detachable suction source, exhausting the exhaled air from said area through the catheter tube and suction source and drawing fresh air into the area through the material of the mask.

13. A disposable mask and suction catheter, comprising: a disposable pervious mask having a front side and a back side, the back side being disposed in contact with a user's face during use and allowing the user to breath through the mask; and a length of relatively inexpensive lightweight suction catheter tubing having a first and a second end, the first end being removably attachable to a suction source for removing exhaled air and the second end being in communication with the back side of the mask to receive exhaled air from the user.

14. A disposable mask and suction catheter, comprising: a disposable pervious mask having a front side and a back side, the back side being disposed in contact with a user's face during use and allowing a user to breather through the mask during an operation; and
   a length of relatively inexpensive lightweight suction catheter tubing having a first and a second end, the first end adapted to be connected to an available hospital operating room wall suction source for removing exhaled air, and the second end being in communication with the back side of the mask to receive exhaled air from a user.

15. The disposable mask and suction catheter as set forth in claim 14, further comprising means for removably attaching the catheter tube to a user's clothing.

16. The disposable mask and suction catheter as set forth in claim 15, wherein the removable attaching means includes a clip.

17. The disposable mask and suction catheter as set forth in claim 14, wherein the second end of the catheter tubing is fixedly attached to the back side of the mask.

18. The disposable mask and suction catheter as set forth in claim 17, wherein the second end of the catheter tubing is fixedly attached to the back side of the mask by an adhesive tape.

19. The disposable mask and suction catheter as set forth in claim 14, further comprising flow rate adjusting means, attached to the catheter tubing, for adjusting a flow rate caused by the available hospital operating room wall suction source.

20. The disposable mask and suction catheter as set forth in claim 19, wherein the flow rate adjusting means includes an openable and closable opening in line with the catheter tubing such that the available hospital operating room wall suction source tends to draw more air through the opening, when opened, than through the second end of the catheter tubing.

21. The disposable mask and suction catheter as set forth in claim 19, wherein the flow rate adjusting means includes a valve.

22. The disposable mask and suction catheter as set forth in claim 20, wherein the flow rate adjusting means includes a needle valve.

23. The disposable mask and suction catheter of claim 14, wherein the catheter tube is a suction catheter of about 14 French diameter.

24. A method of removal of stale, humid air from a surgical mask in use as in claim 14, comprising the attachment of the first end of the suction catheter tubing to an available hospital operating room wall suction source.

25. The disposable mask and suction catheter as set forth in claim 14, wherein the available hospital operating room wall suction source entails a vacuum force between 15–23" of mercury.

26. A method of removal of exhaled air from an area between a disposable mask and the face of the mask wearer, said mask having a suction catheter tube of about 14 French diameter attached at a second end to the mask, said second end of the catheter tube in communication with a backside of the mask for exhaust of said exhaled air, including attaching the first end of said catheter tube to an available, non-detachable, hospital operating room wall suction source, exhausting the exhaled air from said area through the catheter tube and the available hospital operating room wall suction source and drawing fresh air into the area through the material of the mask.

27. A disposable mask and suction catheter, comprising: a disposable pervious mask having a front side and a back side, the back side being disposed in contact with a user's face during use and allowing the user to breath through the mask; and
   a length of relatively inexpensive lightweight suction catheter tubing having a first and a second end, the first end being removably attachable to an available hospital operating room wall suction source for removing exhaled air and the second end being in communication with the back side of the mask to receive exhaled air from the user.

28. A patient breathing aid, including a mask adapted to fit over the wearer's mouth and nose and defining a volumetric zone between the mask and the wearer's face, said mask comprising at least one layer of pervious material permitting the wearer to inhale and exhale therethrough and means for attaching the mask to the face of the wearer, and a tubing of less than about 4 mm internal diameter in communication on one end with the volumetric zone of the mask and the other end adaptable to an available, nondetachable gas supply source, said gas being selected from the group of clean, dry air and oxygen.

29. The patient breathing aid of claim 28, including a flow rate adjusting means in line with said tubing for adjusting the flow of said gas to the volumetric zone of the mask from said available gas supply source.

30. A method of aiding patient breathing comprising supplying a flow of clean, dry air from a stationary supply source via a flexible plastic tubing to a volumetric zone between a disposable air permeable mask and the face of the mask wearer and adjusting the flow of air to said mask to substantially scavenge exhaled carbon dioxide and moisture laden air from the zone through the permeable mask material prior to the wearer's next inhalation.

31. A process of aiding a patient in breathing, comprising the steps of:
   (a) attaching a disposable mask substantially of nonwoven material to the face of the patient, covering the nose and mouth of the patient, said mask material being permeable to air and water vapor, said mask having one end of a flexible plastic tubing of less than about 4 mm internal diameter in communication with a volumetric zone formed by the mask over the nose and mouth of the wearer;
   (b) connecting the other end of said tubing to an available air supply; and (c) adjusting the flow of air from the supply to substantially scavenge exhaled carbon dioxide and moisture laden air from the volumetric zone prior to the patient's next inhalation.

32. The process of claim 31, wherein the tubing is from about 1.6 mm to about 2.8 mm.

33. A disposable mask of at least one layer of nonwoven fibrous material, said layer of material permeable to air and water vapor but inhibiting to fluid flow therethrough, said mask material having an air permeance of between 350 and 4600 $m^{-6}$/Pa.S and a flexible plastic tubing of internal diameter of less than about 4 mm in communication on one end with a face side of the mask in the volumetric zone created by the mask and nose and mouth of the mask wearer and a stationary source of air supply on the other end.

34. A disposable mask assembly comprising a mask of at least one layer of nonwoven fibrous material, said layer of material permeable to air and water vapor but inhibiting to fluid flow therethrough, said mask material having an air permeance of between 350 and 4600 $m^{-6}$/Pa.S and a flexible plastic tubing of internal diameter of less than about 10 mm in communication on one end with a face side of the mask in the volumetric zone created by the mask and nose and mouth of the mask wearer, the other end of the tubing alternatively adaptable to a stationary vacuum source or stationary positive pressured gas source.

35. The mask of claim 33 or claim 34, wherein the tubing is from about 1.6 mm to about 2.8 mm.

36. The aid of claim 28 or claim 30, wherein the tubing is from about 1.6 mm to about 2.8 mm.

37. A respiratory mask assembly comprising a disposable mask having at least one layer of air and water vapor permeable nonwoven material having liquid flow inhibiting properties, said material having an air permeance of between about 350 and 4600 m-6/Pa.S and a flexible plastic tubing, the second end of said tubing being cooperatively connected to the inner surface of the mask in the area of the nasal and mouth area of the wearer when in place, said flexible plastic tubing having an internal diameter of between about 1.6 and 3.6 mm and of a determined length; the first end being connected in use to a vacuum system of about 15–20 inches mercury.

38. A method of use of the respiratory mask assembly of claim 37, including aspirating between 150 and 600 cubic centimeters per second through said tubing.

39. The respiratory mask assembly of claim 37 further including said mask when in operating having a comfort level of at least 2.

* * * * *